United States Patent
Couture

(10) Patent No.: US 11,833,063 B2
(45) Date of Patent: Dec. 5, 2023

(54) SOFT TISSUE BALANCING IN ROBOTIC KNEE SURGERY

(71) Applicant: Exactech, Inc., Gainesville, FL (US)

(72) Inventor: Pierre Couture, Montreal (CA)

(73) Assignee: Exactech, Inc., Gainesville, FL (US)

( * ) Notice: Subject to any disclaimer, the term of this patent is extended or adjusted under 35 U.S.C. 154(b) by 42 days.

(21) Appl. No.: 17/345,918

(22) Filed: Jun. 11, 2021

(65) Prior Publication Data
US 2022/0133505 A1   May 5, 2022

Related U.S. Application Data

(63) Continuation of application No. 16/262,465, filed on Jan. 30, 2019, now abandoned.
(Continued)

(51) Int. Cl.
*A61F 2/46* (2006.01)
*A61B 34/30* (2016.01)
(Continued)

(52) U.S. Cl.
CPC ............ *A61F 2/4657* (2013.01); *A61B 34/30* (2016.02); *A61F 2/461* (2013.01); *A61F 2/4684* (2013.01);
(Continued)

(58) Field of Classification Search
CPC ...... A61F 2/461; A61F 2/4684; A61F 2/4627; A61F 2002/467; A61F 2002/4633;
(Continued)

(56) References Cited

U.S. PATENT DOCUMENTS

| | | |
|---|---|---|
| 4,501,266 A | 2/1985 | McDaniel |
| 5,470,354 A | 11/1995 | Hershberger et al. |
| | (Continued) | |

FOREIGN PATENT DOCUMENTS

| | | |
|---|---|---|
| AU | 2019214335 A1 | 7/2020 |
| CN | 1810208 A | 8/2006 |
| | (Continued) | |

OTHER PUBLICATIONS

"U.S. Appl. No. 17/345,947, Preliminary Amendment filed Mar. 2, 2022", 6 pgs.
(Continued)

*Primary Examiner* — Anu Ramana
(74) *Attorney, Agent, or Firm* — GREENBERG TRAURIG, LLP

(57) ABSTRACT

A system and method may be used to evaluate soft tissue. A knee arthroplasty soft tissue evaluation may use an adjustable spacer, such as varying sized physical spacers or an inflatable bladder, along with a sensor to measure force, pressure, gap distance, or the like during a range of motion test. A method may include maintaining an equal pressure or gap distance for a medial component and a lateral component of an adjustable spacer during a range of motion test. Information, including, for example a maximum or minimum gap distance or pressure may be determined during the range of motion test. The determined information may be output for display or used to update a surgical plan.

18 Claims, 17 Drawing Sheets

Related U.S. Application Data

(60) Provisional application No. 62/697,227, filed on Jul. 12, 2018, provisional application No. 62/625,706, filed on Feb. 2, 2018.

(51) Int. Cl.
  *A61B 34/00* (2016.01)
  *A61B 90/00* (2016.01)
  *A61B 34/20* (2016.01)
  *A61B 34/10* (2016.01)
  *A61B 17/00* (2006.01)

(52) U.S. Cl.
  CPC .............. *A61B 2017/00221* (2013.01); *A61B 2034/105* (2016.02); *A61B 2034/108* (2016.02); *A61B 2034/2048* (2016.02); *A61B 2034/2055* (2016.02); *A61B 2034/252* (2016.02); *A61B 2034/256* (2016.02); *A61B 2090/061* (2016.02); *A61B 2090/065* (2016.02); *A61F 2002/467* (2013.01); *A61F 2002/4633* (2013.01)

(58) Field of Classification Search
  CPC .............. A61B 34/30; A61B 2090/065; A61B 2034/105; A61B 2034/2055; A61B 2034/252; A61B 2090/061
  See application file for complete search history.

(56) References Cited

U.S. PATENT DOCUMENTS

| | | | |
|---|---|---|---|
| 5,682,886 A * | 11/1997 | Delp | A61B 90/36 600/407 |
| 5,733,292 A | 3/1998 | Gustilo et al. | |
| 6,859,661 B2 | 2/2005 | Tuke | |
| 7,604,637 B2 | 10/2009 | Johnson et al. | |
| 7,819,881 B2 | 10/2010 | Stone et al. | |
| 8,337,508 B2 | 12/2012 | Lavallee et al. | |
| 8,652,148 B2 | 2/2014 | Zuhars | |
| 8,656,790 B2 | 2/2014 | Amirouche | |
| 8,814,877 B2 * | 8/2014 | Wasielewski | A61B 17/00 606/91 |
| 9,259,278 B2 | 2/2016 | Jensen | |
| 9,364,294 B2 | 6/2016 | Razzaque et al. | |
| 9,433,471 B2 | 9/2016 | Zuhars | |
| 9,572,588 B2 | 2/2017 | Fisher et al. | |
| 9,808,356 B2 | 11/2017 | Haight et al. | |
| 10,136,951 B2 | 11/2018 | Razzaque et al. | |
| 10,136,952 B2 | 11/2018 | Couture et al. | |
| 10,194,991 B2 | 2/2019 | Bonny et al. | |
| 10,456,263 B2 | 10/2019 | Bojarski et al. | |
| 2002/0052606 A1 * | 5/2002 | Bonutti | A61B 17/0401 606/88 |
| 2004/0236424 A1 | 11/2004 | Berez et al. | |
| 2004/0243148 A1 | 12/2004 | Wasielewski | |
| 2004/0254771 A1 * | 12/2004 | Riener | G09B 23/32 703/7 |
| 2005/0027226 A1 | 2/2005 | Stutz et al. | |
| 2005/0251148 A1 | 11/2005 | Friedrich et al. | |
| 2006/0241569 A1 * | 10/2006 | DiSilvestro | A61F 2/461 606/1 |
| 2007/0198022 A1 | 8/2007 | Lang et al. | |
| 2007/0219561 A1 | 9/2007 | Lavallee et al. | |
| 2007/0234819 A1 | 10/2007 | Amirouche et al. | |
| 2007/0244488 A1 | 10/2007 | Metzger et al. | |
| 2009/0018544 A1 | 1/2009 | Heavener | |
| 2009/0299228 A1 | 12/2009 | Lozier et al. | |
| 2010/0249658 A1 | 9/2010 | Sherman | |
| 2010/0249787 A1 | 9/2010 | Roche | |
| 2010/0249791 A1 | 9/2010 | Roche | |
| 2011/0029093 A1 | 2/2011 | Bojarski | |
| 2012/0158152 A1 | 6/2012 | Claypool et al. | |
| 2013/0013076 A1 | 1/2013 | Fisher et al. | |
| 2013/0197542 A1 | 8/2013 | Bonutti | |
| 2013/0211531 A1 | 8/2013 | Steines et al. | |
| 2013/0261505 A1 | 10/2013 | Sherman | |
| 2013/0267959 A1 | 10/2013 | Engh et al. | |
| 2013/0317344 A1 | 11/2013 | Borus et al. | |
| 2013/0331850 A1 | 12/2013 | Bojarski et al. | |
| 2015/0057758 A1 | 2/2015 | Axelson, Jr. et al. | |
| 2015/0105782 A1 | 4/2015 | D'lima et al. | |
| 2015/0106024 A1 * | 4/2015 | Lightcap | A61B 5/4851 600/587 |
| 2016/0278754 A1 | 9/2016 | Todorov et al. | |
| 2016/0278944 A1 | 9/2016 | D'lima et al. | |
| 2017/0360512 A1 | 12/2017 | Couture et al. | |
| 2019/0053859 A1 | 2/2019 | Couture et al. | |
| 2019/0167447 A1 | 6/2019 | Angibaud | |
| 2019/0240045 A1 | 8/2019 | Couture | |
| 2019/0240046 A1 | 8/2019 | Couture | |
| 2022/0133506 A1 | 5/2022 | Couture | |

FOREIGN PATENT DOCUMENTS

| | | |
|---|---|---|
| CN | 103957992 A | 7/2014 |
| CN | 105682612 A | 6/2016 |
| CN | 107530097 A | 1/2018 |
| CN | 111615359 A | 9/2020 |
| CN | 111629685 A | 9/2020 |
| EP | 1226788 A1 | 7/2002 |
| WO | 03/079940 A2 | 10/2003 |
| WO | 2009/046547 A1 | 4/2009 |
| WO | WO-2009046547 A1 | 4/2009 |
| WO | 2010/015877 A1 | 2/2010 |
| WO | WO-2010015877 A1 | 2/2010 |
| WO | 2014/144107 A1 | 9/2014 |
| WO | WO-2014144107 A1 | 9/2014 |
| WO | WO-2014149079 A1 | 9/2014 |
| WO | 2017/178951 A1 | 10/2017 |
| WO | WO-2017178951 A1 | 10/2017 |
| WO | WO-2019148284 A1 | 8/2019 |

OTHER PUBLICATIONS

"Australian Application Serial No. 2019214338, Response Filed Apr. 28, 2022 to First Examination Report dated May 21, 2021", 12 pgs.
"Australian Application Serial No. 2019214338, Subsequent Examiners Report dated May 3, 2022", 4 pgs.
"European Application Serial No. 19747760.7, Response filed May 11, 2022 to Extended European Search Report dated Oct. 21, 2021", 23 pgs.
"Canadian Application Serial No. 3,089,218, Examiner's Rule 86(2) Requisition dated Mar. 30, 2022.", 3 pgs.
"European Application Serial No. 19747526.2, Response filed May 9, 2022 to Extended European Search Report dated Oct. 11, 2021", 21 pgs.
"Canadian Application Serial No. 3,088,912, Examiner's Rule 86(2) Requisition dated Jul. 14, 2022", 4 pgs.
"U.S. Appl. No. 16/262,465, Non Final Office Action dated Dec. 16, 2020", 8 pgs.
"U.S. Appl. No. 16/262,465, Response filed Sep. 16, 2020 to Restriction Requirement dated Jul. 22, 2020", 7 pgs.
"U.S. Appl. No. 16/262,465, Restriction Requirement dated Jul. 22, 2020", 5 pgs.
"U.S. Appl. No. 16/262,482, Non Final Office Action dated Dec. 16, 2020", 8 pgs.
"U.S. Appl. No. 16/262,482, Response filed Sep. 16, 2020 to Restriction Requirement dated Jul. 23, 2020", 7 pgs.
"U.S. Appl. No. 16/262,482, Restriction Requirement dated Jul. 23, 2020", 5 pgs.
"Australian Application Serial No. 2019214335, First Examination Report dated Jan. 20, 2021", 4 pgs.
"Australian Application Serial No. 2019214338, First Examination Report dated May 21, 2021", 3 pgs.
"International Application Serial No. PCT/CA2019/050119, International Preliminary Report on Patentability dated Aug. 13, 2020", 6 pgs.

(56) References Cited

OTHER PUBLICATIONS

"International Application Serial No. PCT/CA2019/050119, International Search Report dated Apr. 18, 2019", 3 pgs.
"International Application Serial No. PCT/CA2019/050119, Written Opinion dated Apr. 18, 2019", 4 pgs.
"International Application Serial No. PCT/CA2019/050124, International Search Report dated Apr. 26, 2019", 9 pgs.
"International Application Serial No. PCT/CA2019/050124, Written Opinion dated Apr. 26, 2019", 6 pgs.
"Traditional 510(k) Premarket Notification XO Knee Balancing System", XPANDORTHO, Inc., (Aug. 3, 2016), 1278 pgs.
"XpandOrtho XO Knee Balancing System", XpandOrtho, (Mar. 31, 2017), 13 pgs.
Bhandari, Mohit, et al., "Ligament balancing in total knee arthroplasty", JointEvidence; Lit. No. 1898-e, (Mar. 2009), 44 pgs.
Collo, A., et al., "An Active Tibial Component for Postoperative Fine-Tuning Adjustment of Knee Ligament Imbalance", 2014 5th IEEE RAS & EMBS International Conference on Biomedical Robotics and Biomechatronics (BioRob), (Aug. 2014), pp. 126-131.
Colwell Jr., Clifford W., et al., "Self-Adapting Electronic Intraoperative Ligament Balance Predicts Postoperative Knee Kinematics", ORS 2016 Annual Meeting Poster No. 1876, Shiley Center for Orthopaedic Research & Education, (Mar. 2016), 1 pg.
Colwell, Jr., C.W., et al., "The Electronic Knee", Total Knee Arthroplasty; Chapter 45, (2005), pp. 282-287.
D'lima, Daryl D., et al., "Dynamic Intraoperative Ligament Balancing for Total Knee Arthroplasty", Clinical Orthopaedics and Related Research; No. 463, (Jul. 2007), pp. 208-212.
D'Lima, D., et al., "Novel Electronic Intraoperative Ligament Balance Predicts Postoperateve Knee Kinematecs", Orthopaedic Proceedings vol. 98-B, No. SUPP 7, (Feb. 21, 2018), 3 pgs.
D'Lima, Darryl D., et al., "Intraoperative Measurements and Tools to Assess Stability", Journal of the American Academy of Orthopaedic Surgeons, vol. 25, Supplement 1, (Feb. 2017), pp. S29-S32.
D'Lima, Darryl, et al., "The Science of Knee Ligament Balance", Orthopaedic Proceedings vol. 98-B, No. SUPP 1, (Feb. 21, 2018), 3 pgs.
Fregly, Benjamin J, et al., "Grand Challenge Competition to Predict In Vivo Knee Loads", Journal of Orthopaedic Research, (Apr. 2012), pp. 503-513.
Gerus, Pauline, et al., "Subject-specific knee joint geemetw improves predictions of medial tibiofemoral centact forces", J Biomech.; 46(16), (Nov. 15, 2013), 19 pgs.
Gustke, K.A., et al., "Increased satisfaction after total knee replacement using sensor-guided technology", Bone Joint J; 96-B: No. 16, (Oct. 2014), pp. 1333-1338.
Kirkeng, Bryan, et al., "A multiaxial force-sensing implantable tibial prosthesis", Journal of Biomechanic, vol. 39, Issue 9; https://doi.org/10.1016/j.jbiomech.2005.05.023, (2006), 2 pgs.
Kwak, Dai-Soon, et al., "Development of a Pneumatic Tensioning Device for Gap Measurement during Total Knee Arthroplasty", Clinics in Orthopedic Surgery;4:1, (Sep. 2012), pp. 188-192.
Marmignon, C., et al., "Automated hydraulic tensor for Total Knee Arthroplasty", Int J Medical Robotics and Computer Assisted Surgery 2005;1(4); (www.bjs.co.uk), (Oct. 2005), pp. 51-57.
Nagamine, Ryuji, et al., "Comparison of Values of Joint Gap Distance and Angle After Each Step of Medial Soft-Tissue Release Between Offset and Standard Tensor/Balancers in TKA", Orthopaedic Proceedings vol. 98-B, No. SUPP 3, (Feb. 21, 2018), 3 pgs.
Nielsen, Evan S., et al., "Second-Generation Electronic Ligament Balancing for Knee Arthroplasty: A Cadaver Study", The Journal of Arthroplasty 33, (Fe. 2018), pp. 2293-2300.
Wium, Daniël Jacobus, "Development of a dynamic tensioner device for joint gap stiffness during knee arthroplasty", Stellenbosch University https://scholar.sun.ac.za, (Mar. 2018), 145 pgs.
Zhao, Dong, et al., "In Vivo Medial and Lateral Tibial Loads during Dynamic and High Flexion Activites", Journal of Orthopaedic Research, (May 2007), pp. 593-602.
"Australian Application Serial No. 2019214335, Response filed Jan. 4, 2022 to First Examination Report dated Jan. 20, 2021", 14 pgs.
"Canadian Application Serial No. 3,088,912, Office Action dated Sep. 17, 2021", 5 pgs.
"Canadian Application Serial No. 3,088,912, Response filed Jan. 17, 2022 to Office Action dated Sep. 17, 2021", 16 pgs.
"Canadian Application Serial No. 3,089,218, Office Action dated Sep. 1, 2021", 3 pgs.
"Canadian Application Serial No. 3,089,218, Response filed Dec. 29, 2021 Office Action dated Sep. 1, 2021", 12 pgs.
"European Application Serial No. 19747526.2, Extended European Search Report dated Oct. 11, 2021", 12 pgs.
"European Application Serial No. 19747760.7, Extended European Search Report dated Oct. 21, 2021", 13 pgs.
Damm, P, et al., "Total hip joint prosthesis for in vivo measurement of forces and moments", Medical Engineering & Physics, Butterworth-Heinemann, GB, vol. 32, No. 1, (Jan. 1, 2010), 95-100.

\* cited by examiner

Hall effect sensor provides accurate gap measurements in medial and lateral 2 air chamber allows individual pressure in medial and lateral

SOFT TISSUE BALANCING IN ROBOTIC KNEE SURGERY

CLAIM OF PRIORITY

This application is a continuation of U.S. patent application Ser. No. 16/262,465, filed Jan. 30, 2019, now abandoned, which claims the benefit of priority to U.S. Provisional Applications Nos. 62/625,706, tiled Feb. 2, 2018, titled "SOFT TISSUE BALANCING IN ROBOTIC KNEE SURGERY"; and 62/697,227, filed Jul. 12, 2018, titled "SOFT TISSUE BALANCING IN ROBOTIC KNEE SURGERY"; each of which is hereby incorporated herein by reference in its entirety.

BACKGROUND

Computer-assisted surgery has been developed in order to help a surgeon in altering bones, and in positioning and orienting implants to a desired location. Computer-assisted surgery may encompass a wide range of devices, including surgical navigation, pre-operative planning, and various robotic devices. One area where computer-assisted surgery has potential is in orthopedic joint repair or replacement surgeries. For example, soft tissue balancing is an important factor in articular repair, as an unbalance may result in joint instability. However, when performing orthopedic surgery on joints, soft tissue evaluations are conventionally done by hand, with the surgeon qualitatively assessing the limits of patient's range of motion. The conventional technique may result in errors or lack precision.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods for soft tissue balancing in robotic knee arthroplasty are provided herein. Knee arthroplasty techniques may benefit from the use of a robotic device to assist in the surgery. One aspect of knee arthroplasty includes checking knee alignment and kinematics throughout a range of motion of the knee. As the knee moves, gap distance or tension on ligaments may be measured to determine kinematics and alignment. In an example, a spacer may be inserted into the knee during a range of motion test to maintain a particular tension or gap distance while kinematics or alignment are checked. The spacer may be an electronic device, such as described below, to transmit force or tension information. In another example, the spacer may be adjustable, such that the adjustable spacer may maintain a fixed pressure or gap distance during a range of motion test. In an example, a spacer may maintain different forces or gap distances on a medial versus a lateral side of the knee.

Figure 1:
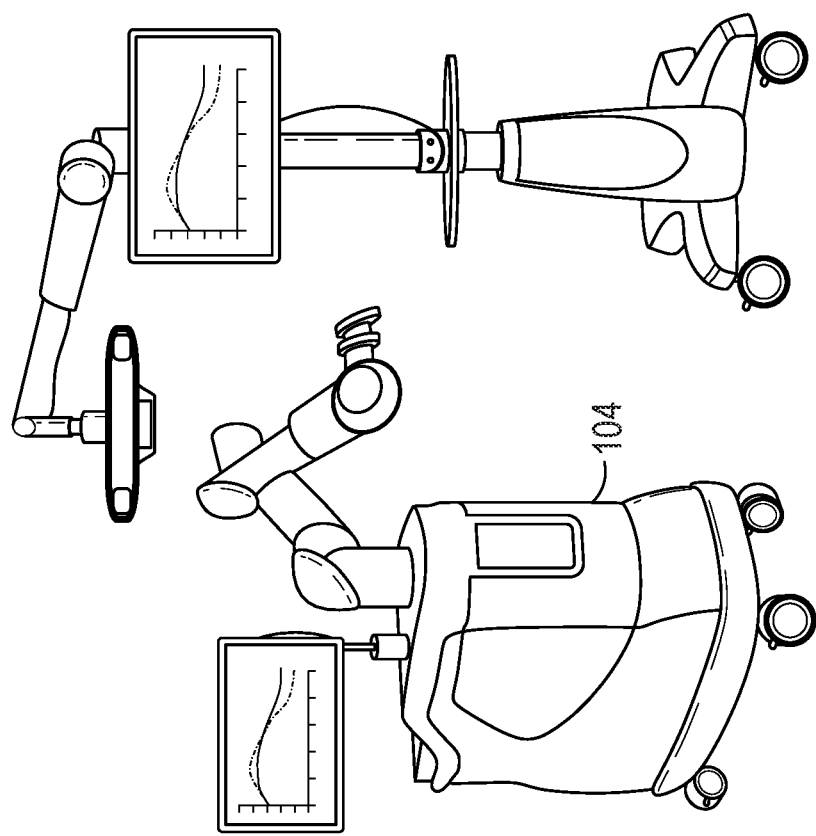
FIG. 1 illustrates a force sensor device used with a robotic arm in accordance with some embodiments.
Figure 1:
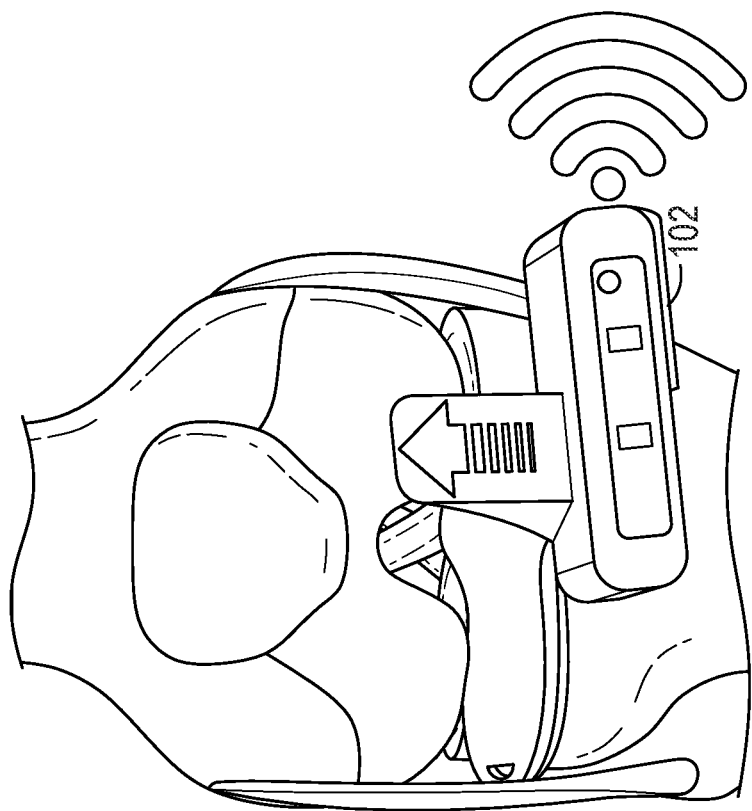

FIG. 1 illustrates a force sensor device used with a robotic arm in accordance with some embodiments. Systems and techniques described herein include adapting for wireless communication an eLibra dynamic knee balancing system provided by Synvasive Technology, Reno, Nev. for use with the Medtech SA ROSA robotic surgical system for total and partial knee arthroplasty.

As shown in FIG. 1, an eLibra device 102 wirelessly transmits force and tension data captured by the eLibra device to a robotic device 104. The eLibra device 102 may track, via onboard accelerometers and gyroscopes, the relative orientation of the eLibra device 102 which, combined with the optical tracking system of the robotic device 104 (e.g., a Medtech ROSA robot) allows a graph to be shown as displayed on FIG. 1 of the forces in the medial and lateral compartments of the knee throughout the range of motion.

The method of balancing the knee in total knee arthroplasty using this combination of eLibra and the ROSA knee application may works as described below.

Figure 2:
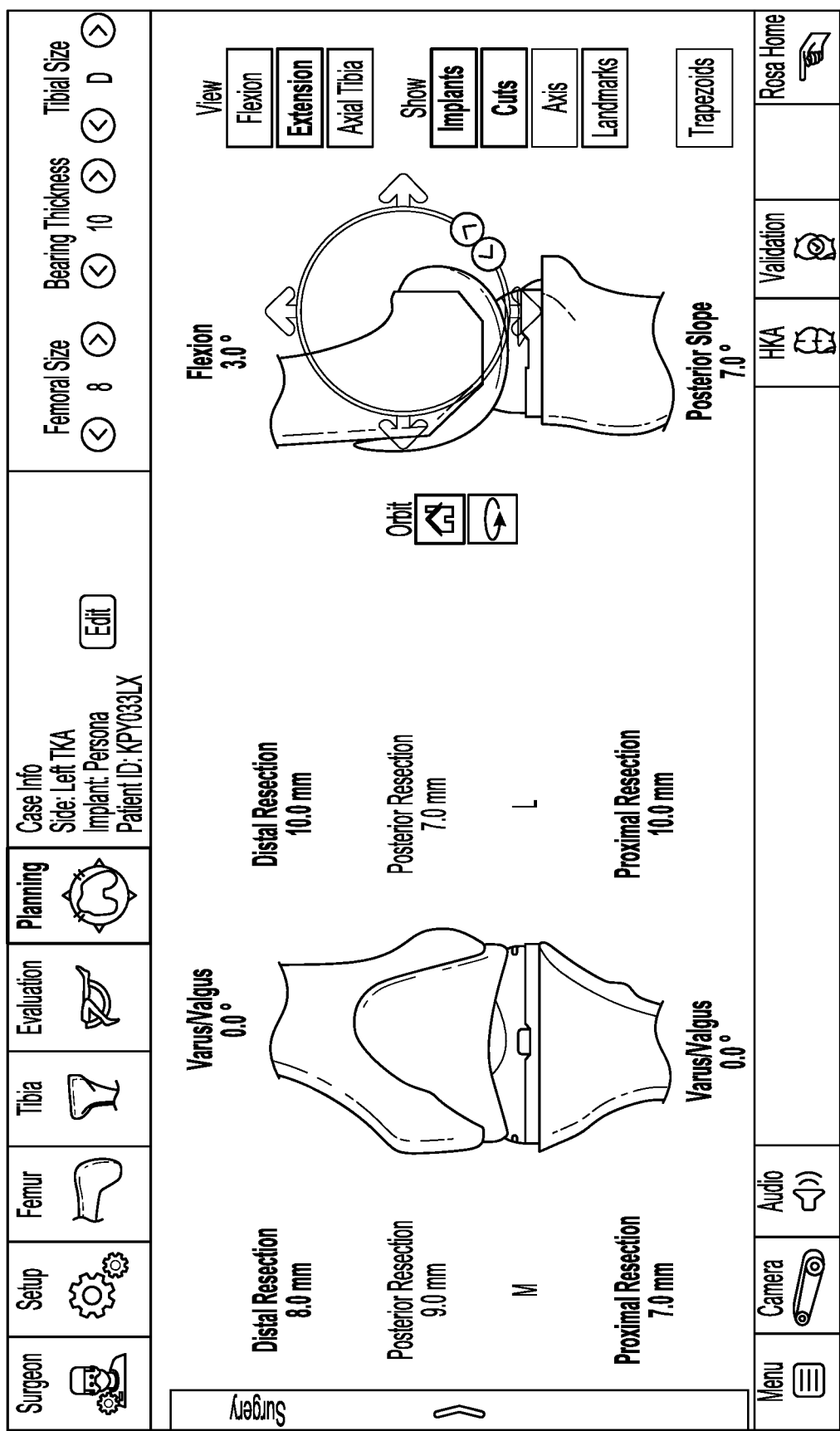
FIGS. 2-3 illustrate surgical planning user interfaces in accordance with some embodiments.

Before performing any of the femoral resections in a knee arthroplasty, the tension of the knee may be checked using a trial device. As shown in FIG. 2, a knee planning screen of a robotic device application is described showing the intended v/v (varus/valgus) of the femoral component, v/v of the tibial cut, the thickness of the distal resection on the medial compartment, the distal resection of the lateral compartment, the proximal resections of both the medial and lateral compartments, or the posterior resections of the medial and lateral compartments, in an example.

The planning screen may show the posterior slope and an angle value for flexion that represents the flexion value used in planning the resection showed in FIG. 2.

Figure 3:
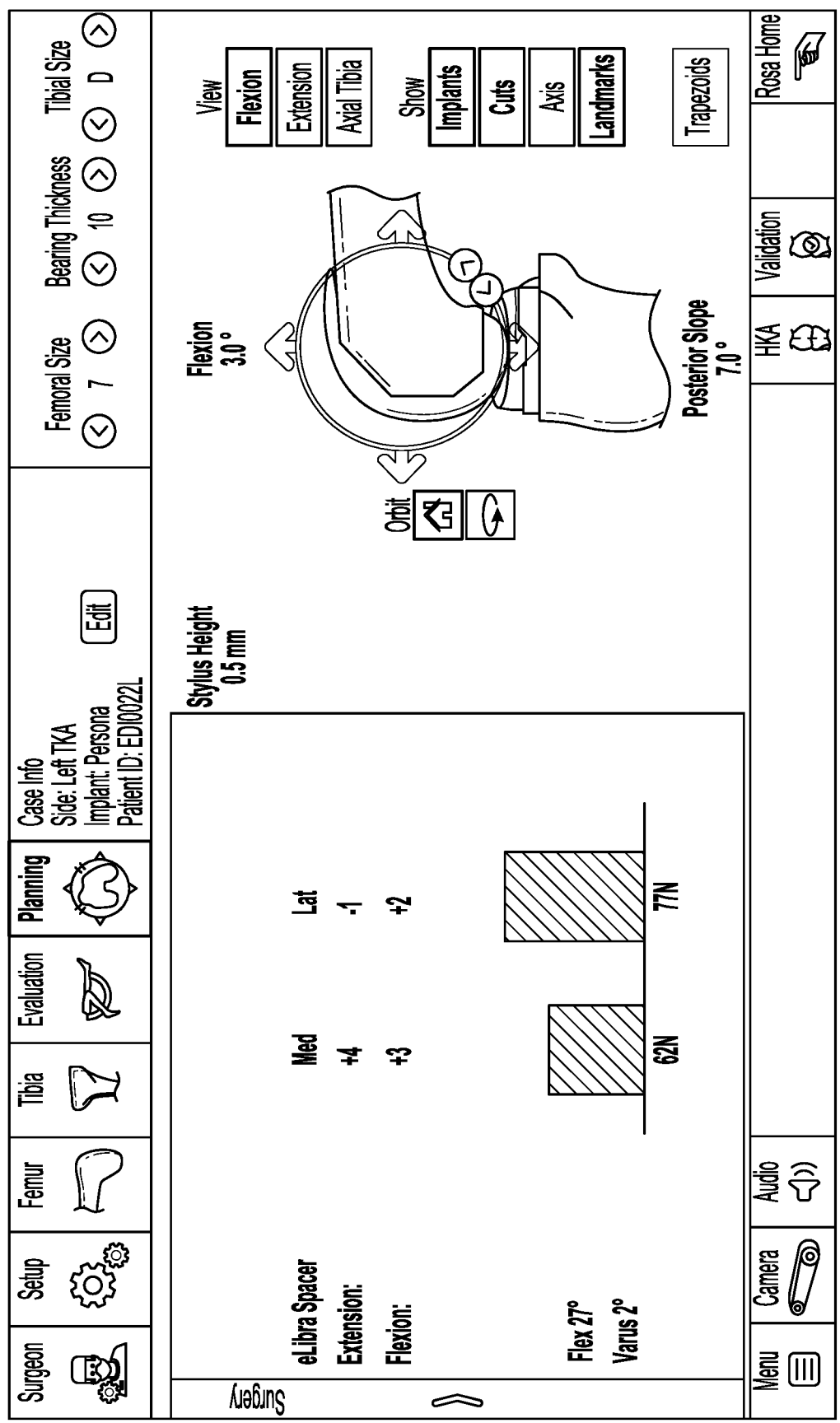

FIG. 3 shows an example of how the information from the eLibra device is incorporated into the planning screen of the robotic knee application. On the left hand side of FIG. 3, the values for the eLibra spacer's recorded force are displayed with 62 Newtons in the medial compartment and 77 Newtons in the lateral compartment. These force values are what are predicted to occur in an example where the surgeon performs resections according to the plans developed herein in FIG. 5 and FIG. 6.

As shown in FIG. 3, in this example, with the knee in 27 degrees of flexion and 2 degree of varus, using a spacer with the eLibra device of size 4 in extension resulted in 62 Newtons of force and using a spacer size of −1 in extension resulted in 77 Newtons of force in this example.

Figure 4:
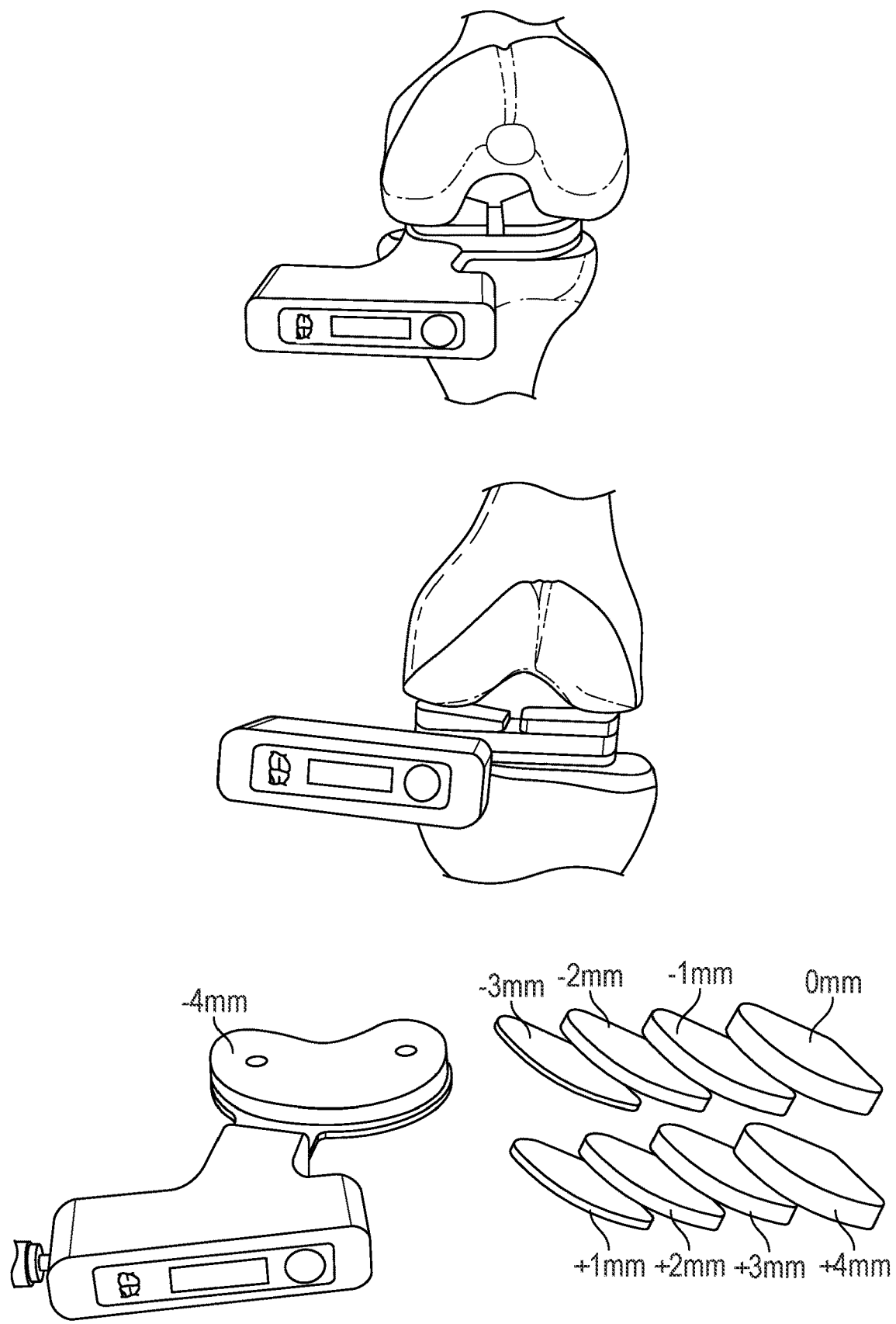
FIG. 4 illustrates an eLibra device with various spacers in accordance with some embodiments.

As shown in FIG. 4, this eLibra spacer values can be accomplished by using shims of variance sizes from −4 mm to −3, −2, −1, 0 mm and so on, to positive one, positive 2, positive 3, positive 4 millimeters.

Figure 9:
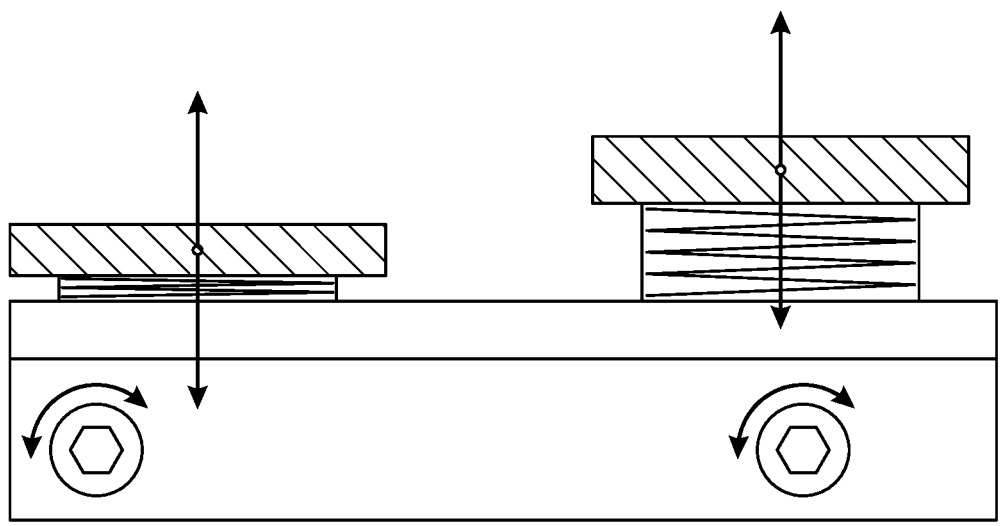
FIG. 9 illustrates an adjustable spacer in accordance with some embodiments.

Alternatively, as shown in FIG. 9, rather than using shims, an adjustable spacer tool, similar to those described in U.S. Pat. No. 9,808,356 to Synvasive Technology may be used to adjust platform heights of the medial and lateral compartments via rotation of a screw or screws. Platform adjustment can also occur via electrometrical means, potentially under control of the robotic device. For example, the a robot system may wirelessly adjust the heights of the medial and lateral compartments of the adjustable spacer as the knee is moved through a range of motion, by detecting the change in orientation of the leg with optical tracking.

Figure 5:
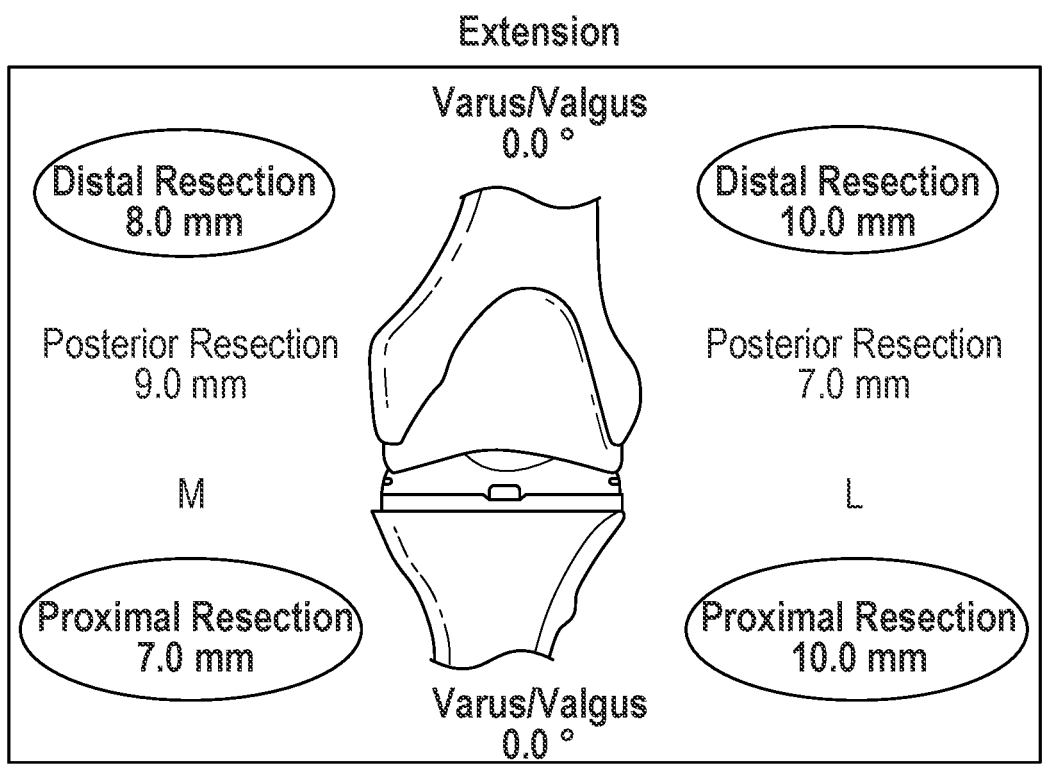
FIGS. 5-6 illustrate calibration user interfaces in accordance with some embodiments.

FIG. 5 shows how the resections of a total knee replacement can be planned using the eLibra spacer and recorded flexion and positioning values.

In this example, on the medial compartment, bone cuts of 15 millimeters total (8.0 distal+7.0 proximal) are planned. With the planned implant size of 19 millimeters the plan would therefore result in an overstuff of the medial compartment of 4 millimeters. Thus, in order to test and measure the tension forces in the medial compartment with this planned resection, the eLibra device should be loaded with a spacer size of 4 millimeters in the medial compartment.

In the lateral compartment, in order to test the tension experienced using these planned resections, the combination of the proximal and distal resections of 10 millimeters each result in planned bone cuts of 20 millimeters total. With a planned implant size of 19 millimeters this would therefore result of laxity and understuff of 1 millimeter in the lateral compartment and a thus −1 millimeter eLibra spacer would be used to measure the forces experienced with this planned cut (FIG. 5) in extension.

Figure 6:
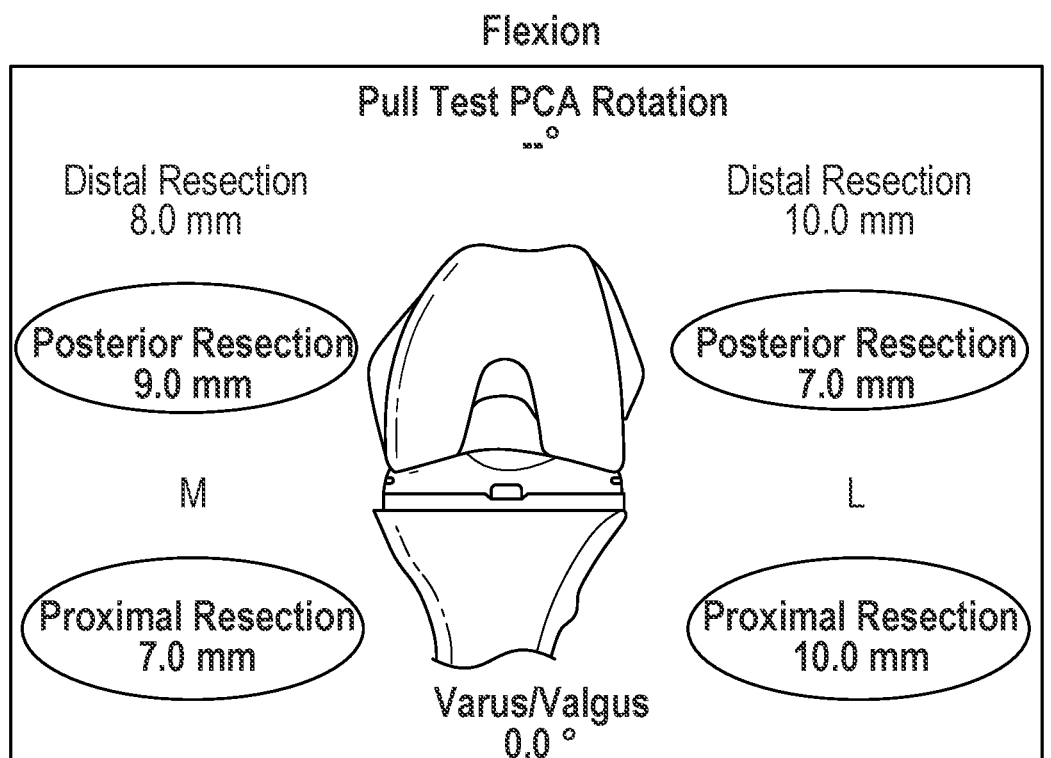

In Flexion as shown in FIG. 6, here the plan calls for a posterior resection of 9 millimeters and a proximal resection of 7 millimeters, thus totaling planned bone cuts in the medial compartment of 16 millimeters. The implant size again being 19 millimeters would result in overstuff of 3 millimeters in the medial compartment and the eLibra spacer then necessary to measure the forces experienced in flexion under these planned resections would be 3 millimeters.

Similarity on the lateral side, with bone cuts planned of 17 millimeters, 10 on the proximal section and 7 on the posterior resection, an implant size of 19 millimeters would therefore result in an overstuff of 2 millimeters in the lateral compartment and therefore an eLibra spacer size of 2 millimeters would be required in order to accurately measure tensions experienced under these planned resections.

The surgeon may adjust the planned resections, test and record the forces captured by the eLibra device in flexion and extension, and then repeat as necessary until the plan results in the desired expected tension values. The surgeon may then perform the femoral resections according to the final plan.

Once the cuts are done, the resections are complete according to the planned values, and tension may be confirmed over the entire range of motion with trial implants such as described in patent applications related to the eLibra device (e.g. U.S. application Ser. No. 13/709,506, incorporated herein by reference in its entirety).

Figure 7:
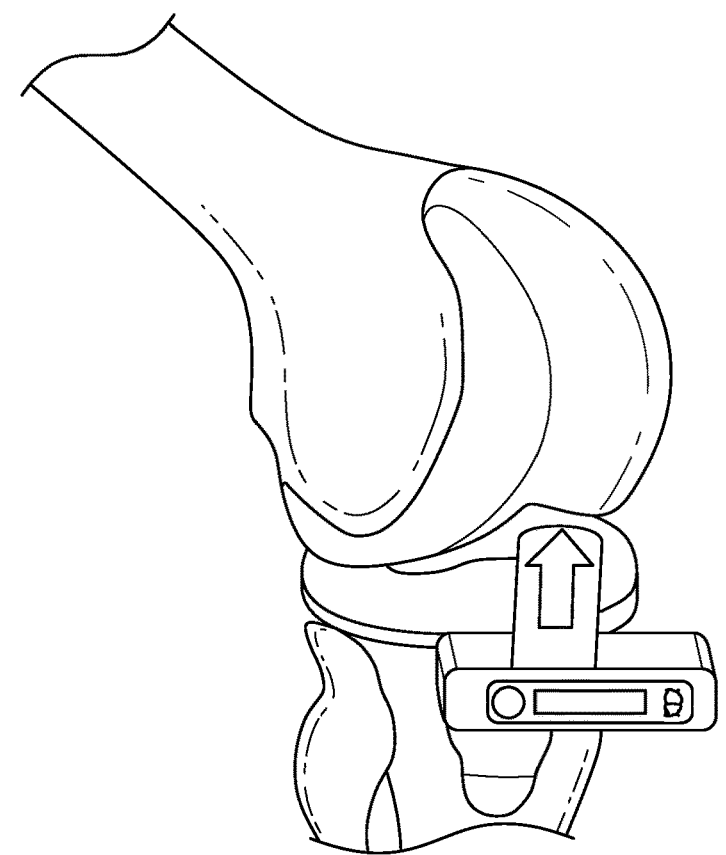
FIG. 7 illustrates a system for using an eLibra device in accordance with some embodiments.
Figure 7:
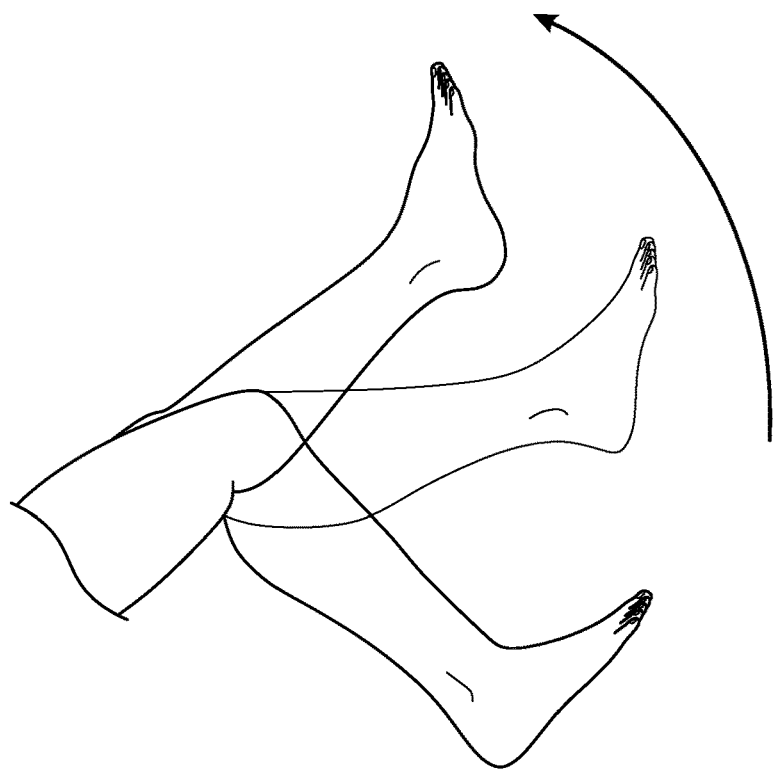
Figure 8:
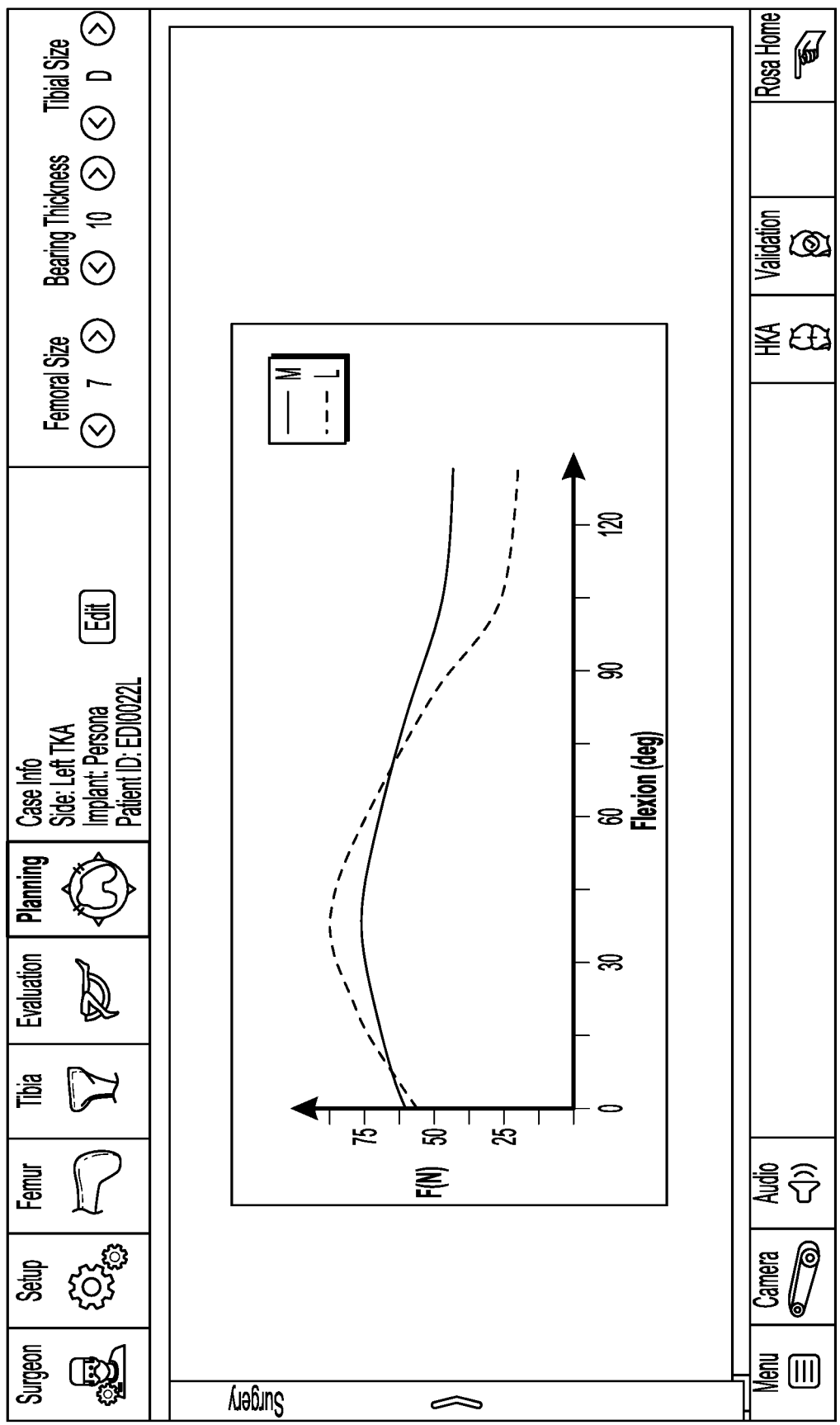
FIG. 8 illustrates a force measurement display user interface in accordance with some embodiments.

As shown in FIG. 7, the eLibra device may be inserted in between the femur and tibia and the patient's leg can be moved throughout the range of motion from flexion to extension and the eLibra device will record (or the CAS system of the ROSA robot will record) force values throughout the range of motion. The force (in Newtons) experienced in the medial compartment is a solid line and the lateral compartment is a dotted line in FIG. 8. The angular values for flexion are captured by virtue of the angular tracking of the eLibra device, which may be performed using an additional sensor, such as an inertial measurement unit (IMU), an accelerometer, a gyroscope, or the like, or the tracking of the robotic deivce (which may track the degree of flexion/extension of the patient's leg by optical tracking of the femur and tibia or using contact with a portion of the knee to track the knee using the robotic device's internal accelerometer or gyroscope).

Systems and methods for using an adjustable spacer for a surgical knee procedure, such as evaluating soft tissue during a knee arthroplasty are described herein. The systems described herein may include using an adjustable spacer with independently adjustable components (e.g., a medial component and a lateral component) for soft tissue evaluation. In an example, the independently adjustable components may be controlled using independent pressure or independent gap distance during a soft tissue evaluation. The adjustable spacer systems and methods described herein may be used with a robotic surgical device.

Robotics offer a useful tool for assisting the surgeon in the surgical field. A robotic device may assist in the surgical field performing tasks such as biopsies, electrode implantation for functional procedures (e.g., stimulation of the cerebral cortex, deep brain stimulation), open skull surgical procedures, endoscopic interventions, other "key-hole" procedures, arthroplasty procedures, such as total or partial knee replacement, hip replacement, shoulder implant procedures, or the like. In an example, a surgical procedure may use a surgical robot. The surgical robot may include a robotic arm for performing operations. A tracking system may be used to determine a relative location of the surgical robot or robotic arm within a coordinate system or a surgical field. The surgical robot may have a different coordinate system or tracking system (e.g., using known movements of the surgical robot). The robotic arm may include an end effector of the robotic arm of the surgical robot, which may use sensors, such as a gyroscope, magnetoscope, accelerometer, etc. In an example, a processor may be used to process information, such as tracking information, operation parameters, applied force, location, or the like.

Figure 10:
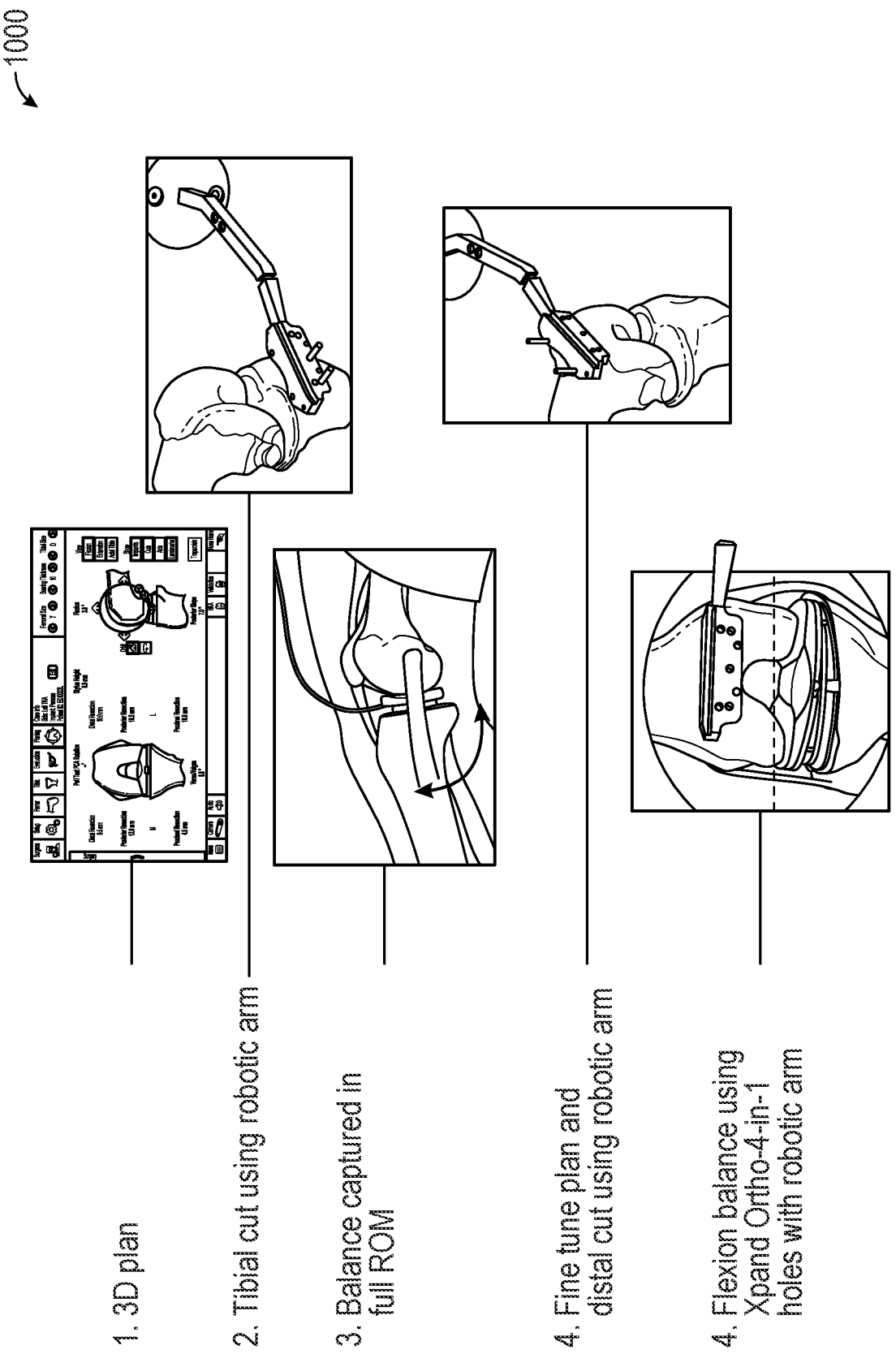
FIG. 10 illustrates a surgical technique in accordance with some embodiments.

FIG. 10 illustrates a surgical technique 1000 in accordance with some embodiments. The technique 1000 uses a robotic surgical device to assist in surgical procedures, such as a resection, a range of motion test, or a soft tissue balancing test. The technique 1000 includes initiating a 3D plan, such as using a user interface of the robotic surgical device (e.g., the Medtech SA ROSA robotic surgical system). The technique 1000 includes an operation to perform a tibial cut, for example using the ROSA or other robotic arm for a total or partial knee arthroplasty. The technique 1000 includes an operation to capture balance during a range of motion test, for example using an inflatable device or a robotic arm. The inflatable device is described in more detail below.

The technique 1000 may include using feedback from the range of motion test to adjust the plan (e.g., automatically change a parameter of the preoperative plan based on the range of motion test, such as balance information, a maximum or minimum distance, range of motion, or angel). The technique 1000 may include performing a distal cut, such as using the robotic arm. The technique 1000 may include evaluating balance in soft tissue, such as flexion or extension balance using the inflatable device, or the robotic arm (e.g., the Rosa robotic arm with a tool attached to an end effector on a distal end of the robotic arm).

In an example, the technique 1000 may include using an optical tracker to track components of a surgery. For example, tracked components may include a femur, a tibia, a robotic arm (e.g., an end effector attached to a distal end of the robotic arm), a tool, or the like. The technique 1000 may include performing a range of motion test to evaluate soft tissue tension, pressure, or gap distance in a knee joint in the range between extension and flexion. Optical trackers may be used to determine various attributes of bones or soft tissue during the range of motion test. For example, distance traveled by the tibia (or femur) throughout the range of motion test, angle of bone during the range of motion test (e.g., maximum flexion angle or maximum extension angle), gap distance at various points or throughout the range of motion test (which may include separate medial and lateral gap distances or a combined or maximum gap distance throughout), or the like.

In an example, the gap distance may be shown on a user interface during the range of motion test. The gap distance may be shown based on a planned resection (or resections, such as a tibial cut or a femoral cut). The planned resection may be shown on the user interface, along with gap distances throughout the range of motion test to display differences or issues that may arise based on the planned resection and the evaluated gap distances. In an example, potential errors arise when using the gap distance with un-resected bone (e.g., the surface of the bone) because the ultimate gap distances for the resected knee do not include the surface errors. For example, osteophytes may cause issues with gap measurement, a varus deformity may impact laxity, an error state may impact gap measurement, or the lateral and medial laxity from a spacer tool may cause measurement issues (e.g., because the ligaments are on the side, the measured laxity may differ from the actual laxity because of the rotation).

The technique 1000 may include establishing the preoperative plan and showing the knee with the planned resections on the user interface. Then as gap distances are determined throughout the range of motion test, the gap distances are displayed on the user interface with the planned resections. This combination of preplanned resection visualization with actual measured gap distance information allows for evaluation of the planned resections with real gap distance feedback. This combination also allows for evaluating the ultimate gap distances with the planned resection rather than gap distances pre-resection, which may not ultimately be accurate. The combination further allows for accurate planning of what the soft tissue balancing (e.g., rotation of the femur relative to the tibia) will be after the planned resection without needing to actually perform the resection. This allows for accurate planning, and modification to the resection may be made.

In an example the technique 1000 may include displaying the measured and actual gap distances with the planned resection by reference to a plane (e.g., the tibial resection plane or a femur horizontal plane). In an example, the femur horizontal plane may be used along with a determined tibial plane a few degrees offset from the femur horizontal plane. In another example, the tibial cut may be performed before the range of motion test. The cut tibial plane may be used, or may be offset by a few mm for the femur plane. In an example, the femur horizontal plane may be used because it is agnostic to movement of the bone, throughout the range of motion (e.g., laxity independent or laxity based on resection, not where bone sits or the femur horizontal plane).

In an example, when expanding the knee, ligaments may be on a side which causes issues with measurement of the gap distance or soft tissue balance. Using the preplanned resection with measured gap distance, and taking into account the plane used for reference, the measurement may be made in a more consistent manner.

In an example, the range of motion test may include registering the tibia with reference to a bone model (e.g., a preoperative plan), and registering a tracker for the tibia (the femur may be registered and tracked as well. The range of motion test is then performed. The tibia is tracked throughout the range of motion test (e.g., by tracking the gap from the planned resection of the femur or tibia to the femur or tibia throughout the range of motion). The gap distance at a point or throughout a range (e.g., a maximum gap distance, an animation of gap distance throughout the range of motion, or a gap distance at a selectable angle of range of motion) may be displayed on the user interface. The user interface may show the gap distance from the preplanned resection to the femur (e.g., instead of from the unresected tibia to the unresected femur).

The gap distance may be measured using the optical trackers, may use an adjustable spacer as described throughout this disclosure, such as an independently adjustable medial and lateral spacer, or a position sensor iAssist). Because a natural rotation may occur during the range of motion test, using an independently adjustable medial and lateral spacer may allow for different gap distances to be measured throughout the range of motion.

Figure 11:
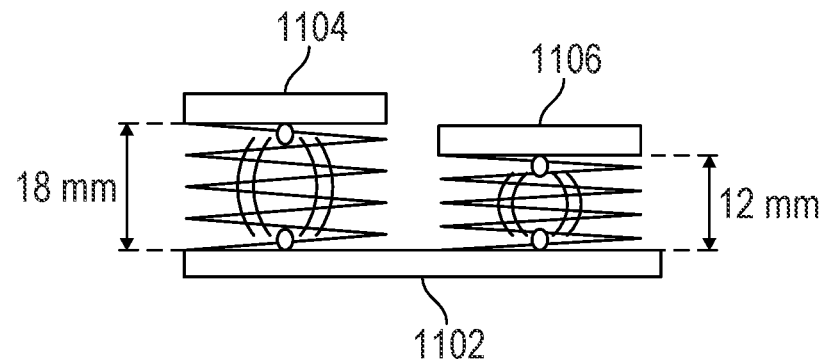
FIG. 11 illustrates an adjustable spacer with independently adjustable medial and lateral components in accordance with some embodiments.
Figure 11:
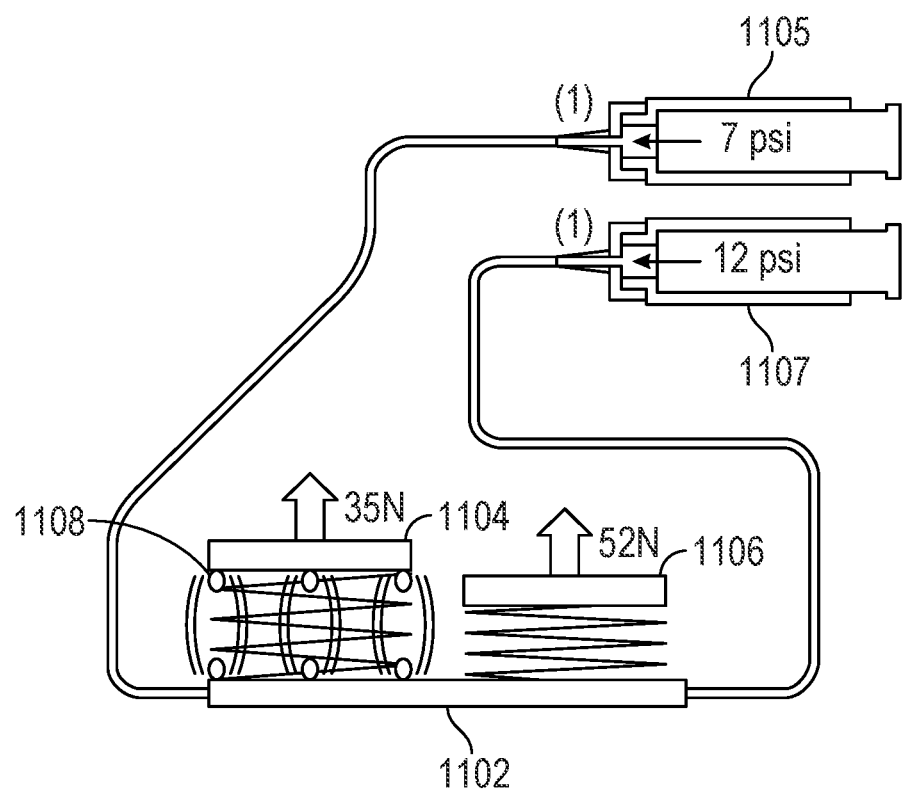

FIG. 11 illustrates an adjustable spacer 1102 with independently adjustable medial and lateral components (1104 and 1106, respectively) in accordance with some embodiments. The adjustable spacer 1102 may be used within a knee, such as for a total or partial knee arthroplasty (e.g., as described above with respect to FIG. 10). The adjustable spacer 1102 may be used to measure, determine, or change a gap distance or pressure difference between a femur and a tibia of a patient. For example, the adjustable spacer 1102 may be placed between the tibia and the femur (e.g., after a tibial resection as described above during technique 1000) and inflated to measure gap distance or pressure, for example throughout a range of motion test.

The adjustable spacer 1102 may be inflated by one or more pumps (e.g., medial pump 1105 or lateral pump 1107, or a single pump with a valve configured to control whether the medial component 1104 or the lateral component 1106 is inflated). The medial component 1104 and the lateral component 1106 of the adjustable spacer 1102 may be independently inflated, adjusted (e.g., undergo an increase in inflation or be deflated), or controlled (e.g., pressure maintenance).

The medial component 1104 and the lateral component 1106 of the adjustable spacer 1102 may be inflated independently to a particular gap distance. For example, as shown in the example in FIG. 11, on the left side the medial component 1104 is inflated to 18 millimeters (mm), and the lateral component 1106 is inflated to 12 millimeters. These gap distances may correspond to internal forces, as shown on the tight side of FIG. 11. The example in FIG. 11 shows a pressure of 35 Newtons (N) in the medial component 1104 and 52 Newtons in the lateral component 1106. The gap distances and forces may further correspond to pressure applied by one or more pumps. For the example of FIG. 11, the medial pump 1105 is applying 7 pounds per square inch (psi) of pressure, corresponding to the 35 N, which may also correspond to 18 mm of gap distance. The lateral pump 1107 applies 12 psi, corresponding to 52 N and 12 mm gap distance. In an example, a surgeon may spread the knee to a desired force with the adjustable spacer 1102 and the femoral rotation required to achieve balance between the medial and lateral sides may be output on a user interface.

The adjustable spacer 1102 may include one or more sensors, such as a Hall effect sensor, to accurately measure the gap distance in the medial component 1104 or the lateral component 1106. For example, the medial component 1104 and the lateral component 1106 may each have a Hall effect sensor to independently measure gap distance in the respective components. In an example, a Hall effect sensor may output a voltage corresponding to a change in magnetic field based on the gap distance. For example, a magnet may be placed on a free end of the medial 1104 or lateral 1106 component, and a Hall effect sensor may be used to determine the change in distance of the component 1104 or 1106 based on the change in magnetic field from the free end being displaced from a base of the adjustable spacer 1102. In this example, the Hall effect sensor may be located on the base of the adjustable spacer 1102 (e.g., on an end opposite the free end of one of the components 1104 or 1106).

The medial pump 1105 or the lateral pump 1107 may be controlled by a pump controller. The pump controller may be coupled to, operated by, or located within a robotic surgical device (e.g., ROSA). For example, the pump controller may be executed using a processor of the robotic surgical device. A user interface of a display of the robotic surgical device (or an external display) may be used to display information (e.g., gap distance, force, pressure, etc.) related to the adjustable spacer 1102, the pump controller, or the medial/lateral pumps 1105/1107.

The gap distance in the medial or lateral component of the adjustable spacer may be determined using a distance sensor, such as a Hall effect sensor. In an example, one distance sensor may be used, such as in a central location of the medial or lateral component. In another example, two distance sensors may be used, such as at either end of the medial or lateral component. In another example, three sensors may be used (e.g., with a sensor shown at 1108), such as one in a central location and two at either end of the medial or lateral component. Other configurations of sensors (e.g., at corners of a component, in the middle of a component) may be used to increase accuracy of gap distance measurements. Other measurement techniques may be used, including using optical tracking of the gap distance, a time-of-flight sensor, a tension sensor, or the like. The sensor measurements for gap distance may be used on the adjustable spacer of FIG. 9 similarly.

Figure 12:
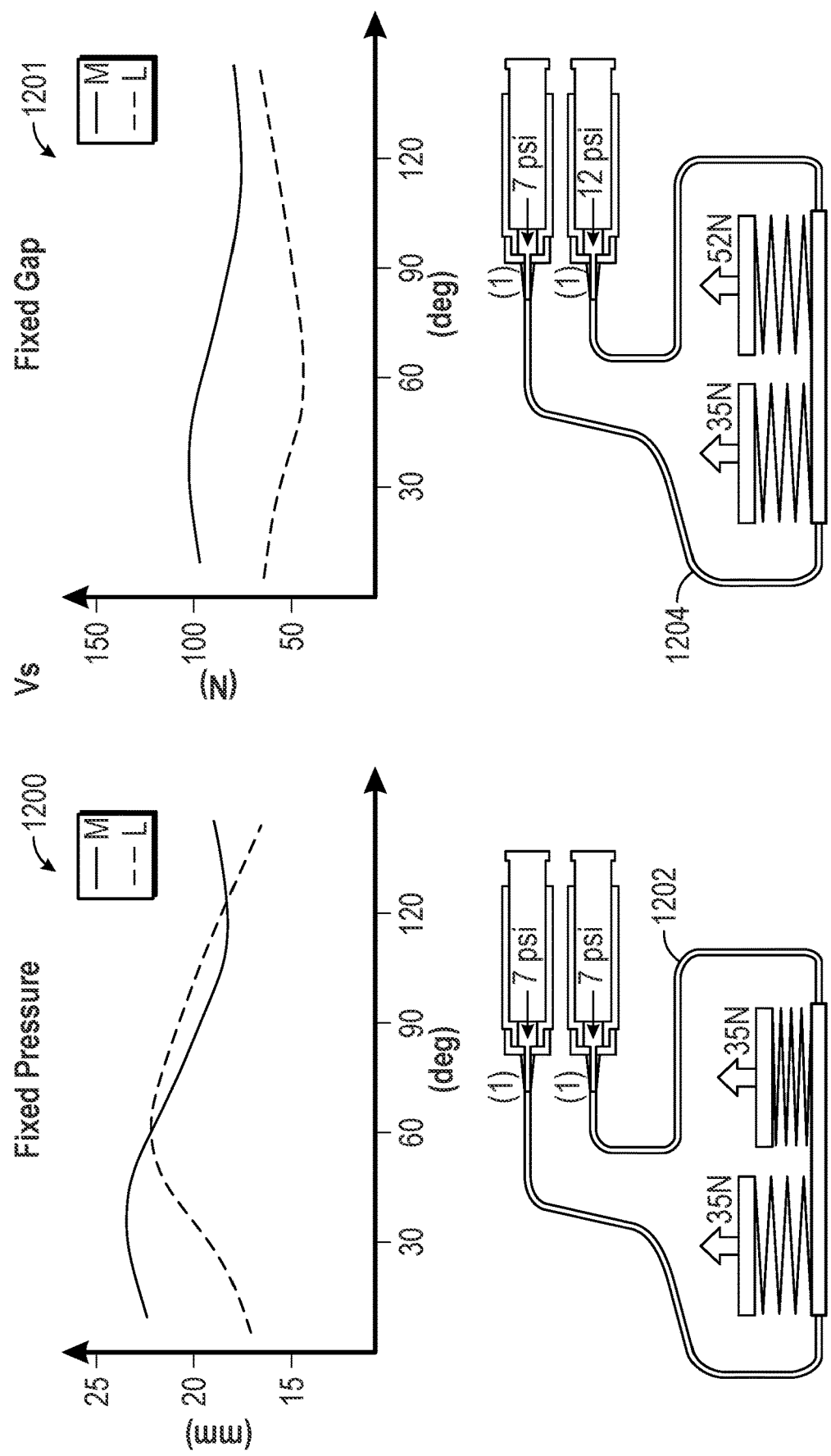
FIG. 12 illustrates an adjustable spacer and graphs showing effects of the adjustable spacer in accordance with some embodiments.

FIG. 12 illustrates an adjustable spacer (1202 and 1204) and graphs 1200 and 1201 showing effects of the adjustable spacer (1202, and 1204) in accordance with some embodiments. The adjustable spacer (1202 and 1204) may be used within a knee, such as for a total or partial knee arthroplasty. The adjustable spacer (1202 and 1204) may be used to measure, determine, or change a gap distance or pressure difference between a femur and a tibia of a patient. For example, the adjustable spacer (1202 and 1204) may be placed between the tibia and the femur (e.g., after a tibial resection) and inflated to measure gap distance or pressure, for example throughout a range of motion test.

The adjustable spacer is shown in a first controlled configuration 1202 corresponding to graph 1200 and a second controlled configuration 1204 corresponding to graph 1201. The first configuration 1202 includes controlling the adjustable spacer such that the pressure in a medial component and a lateral component of the adjustable spacer are fixed. A fixed pressure means that the pressure output from a pump or pumps is equal (e.g., 7 psi) to each component, medial and lateral of the adjustable spacer. Said another way, the medial and lateral components of the adjustable spacer are free to change gap distance (e.g., have unequal gap distance), but have the same pressure applied (air or other fluid applied within a bladder of each component). The fixed pressure may also result in equal force (e.g., 35 N) within each component (e.g., as applied to a free end from a fixed end, shown in FIG. 12 with an upward arrow).

Graph 1200 illustrates changes in gap distance for the fixed pressure adjustable spacer 1202 throughout a range of motion test. Graph 1200 has an x-axis illustrating degrees of the range of motion test (e.g., starting at zero degrees for a fully extended knee, and moving up in degrees towards flexion). The y-axis of graph 1200 illustrates a gap distance (e.g., in the example shown in FIG. 12, fluctuating between 15 and 25 mm). The gap distance is shown on graph 1200 in the medial component (M) and the in the lateral component (L) of the adjustable spacer 1202 separately. The graph 1200 may be output to a user interface on a display (e.g., a display of a robotic surgical system) for evaluation by a surgeon. In an example, a maximum or minimum gap distance for each component may be determined from the range of motion test. The maximum or minimum gap distance (in either component or a maximum or minimum in both components) may be used to adjust a surgical plan (e.g., a preoperative plan), such as by changing a parameter for a planned resection of the femur, changing an implant size, or adjusting soft tissue (e.g., releases). The changes to the preoperative plan may be made automatically, for example changing a parameter of a planned resection by a robotic arm.

The second configuration 1204 includes controlling the adjustable spacer such that the gap distances in the medial component and the lateral component of the adjustable spacer are fixed. A fixed gap distance means that the pressure output from a pump or pumps varies (e.g., 7 psi and 12 psi as shown in FIG. 12) to each component, medial and lateral of the adjustable spacer. The medial and lateral components of the adjustable spacer are thus fixed to a certain gap distance, which may be determined as part of a preoperative plan or interoperative change to a preoperative plan. The change in pressure may be adjusted during a range of motion test to retain the equal gap distance between the two components. The change in pressure may correspond to a change in force (e.g., 35 N for 7 psi and 52 N for 12 psi), as applied to a free end from a fixed end, shown in FIG. 12 with an upward arrow.

Graph 1201 illustrates changes in pressure for the fixed equal gap distance in components of the adjustable spacer 1202 throughout a range of motion test. Graph 1201 has an x-axis illustrating degrees of the range of motion test (e.g., starting at zero degrees for a fully extended knee, and moving up in degrees towards flexion). The y-axis of graph 1201 may illustrate a pressure (e.g., applied from a pump) or a force applied by the or within each component (e.g., in the example shown in FIG. 12, a force is illustrated). The pressure change is shown on graph 1201 in the medial component (M) and the in the lateral component (L) of the adjustable spacer 1202 separately. The graph 1201 may be output to a user interface on a display (e.g., a display of a robotic surgical system) for evaluation by a surgeon. In an example, a maximum or minimum pressure for each component may be determined from the range of motion test. The maximum or minimum pressure (in either component or a maximum or minimum in both components) may be used to adjust a surgical plan (e.g., a preoperative plan), such as by changing a parameter for a planned resection of the femur, changing an implant size, or adjusting soft tissue (e.g., releases). The changes to the preoperative plan may be made automatically, for example changing a parameter of a planned resection by a robotic arm.

In an example, only one side of the adjustable spacer 1202 (e.g., medial or lateral) may be inflated. The singly inflated side may be used to perform a stress test for the knee joint. During a stress test (which may be performed before or after a tibial cut), the lateral or the medial side may be inflated to assess ligament tension and find a gap distance for that side. The stress test for one or both sides (medial and lateral) inflated, one at a time, may be conducted instead of or in addition to a range of motion test with both sides (medial and lateral) inflated.

Figure 13:
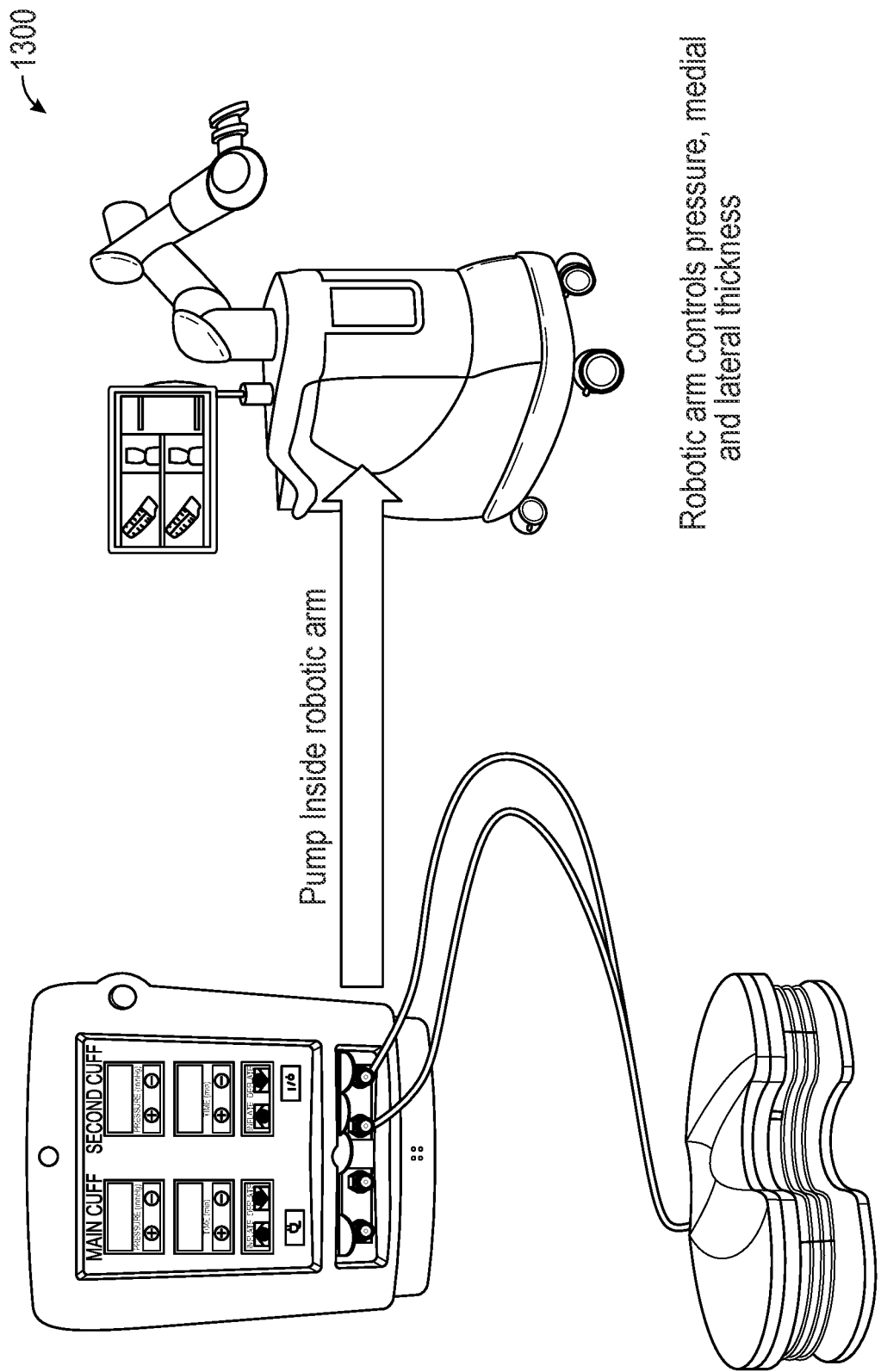
FIG. 13 illustrates a system for using an adjustable spacer with a robotic surgical device in accordance with some embodiments.

FIG. 13 illustrates a system 1300 for using an adjustable spacer with a robotic surgical device in accordance with some embodiments. The system 1300 may include a robotic surgical system or device (e.g., a ROSA robotic surgical system), which may include a user interface and a robotic arm. The robotic surgical system or device may include a pump, be configured to hold or support a pump, interface with a pump, or the like. In another example, the system 1300 may include a pump separate from the robotic surgical system or device. The pump (which may include more than one pump) may be used to control an adjustable spacer. In the example where the pump is controlled by the robotic system or device, a processor of the robotic system or device may control pressure output to one or more components of the adjustable spacer. The robotic surgical system or device may be used to control the pump during a range of motion test, such as to evaluate gap distance or pressure in a medial or lateral component of the adjustable spacer.

Figure 14:
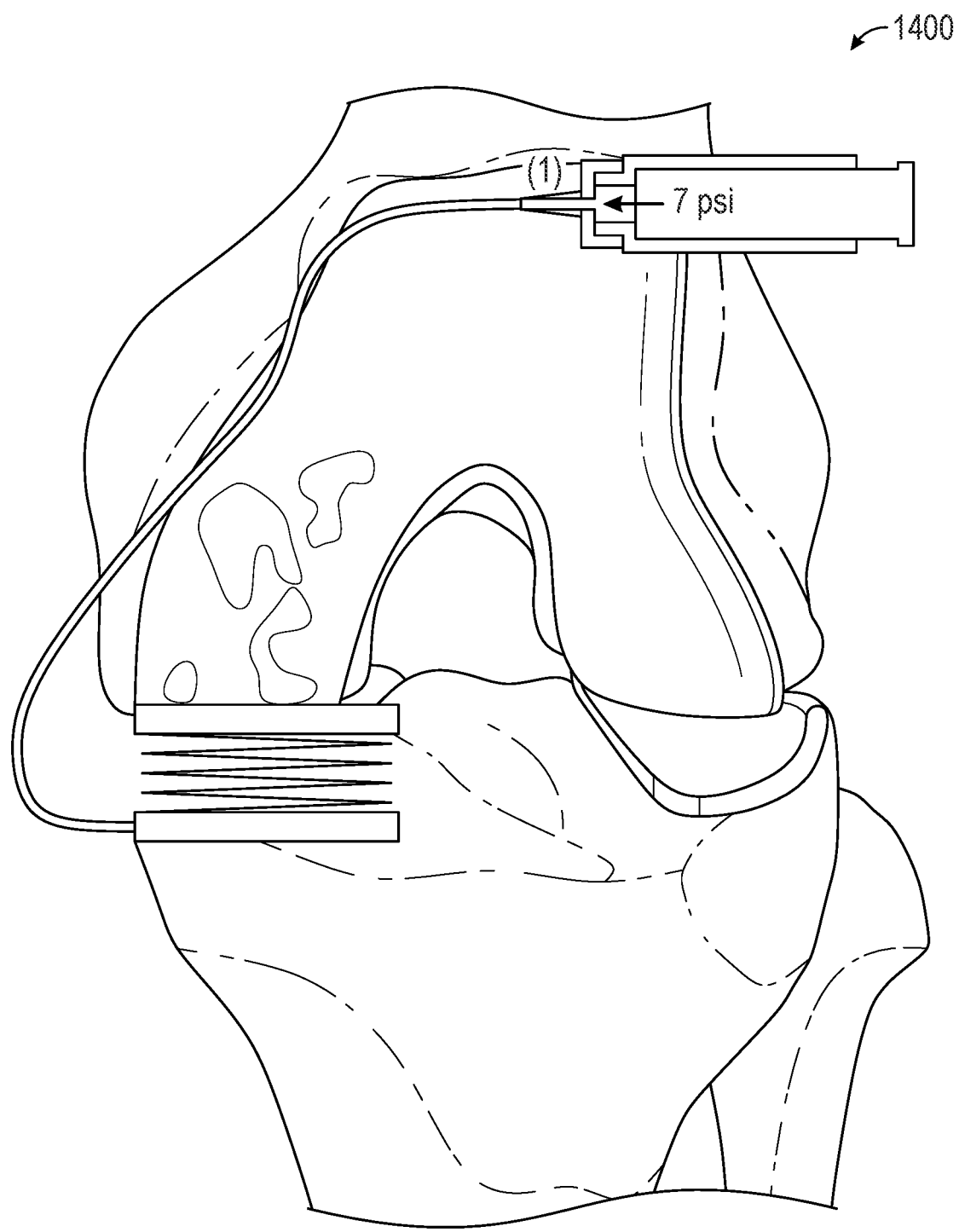
FIG. 14 illustrates a unicondylar adjustable spacer used in a partial knee arthroplasty in accordance with some embodiments.

FIG. 14 illustrates a unicondylar adjustable spacer used in a partial knee arthroplasty in accordance with some embodiments. The diagram 1400 illustrated in FIG. 14 shows a unicondylar adjustable spacer, which may be inflated or adjusted using a pump (e.g., controlled by a robotic surgical system). In another example, an adjustable spacer with both medial and lateral components may be used, such as by only inflating one side when used with a partial knee arthroplasty or when doing a unicondylar surgery on both the medial and the lateral sides of a single knee. The singularly inflated component may be used during a range of motion test, holding gap distance to a specific gap distance or holding pressure to a specific pressure (e.g., a specific gap distance or specific pressure from a surgical plan). A minimum tension may be determined during the range of motion test. The minimum tension may be output, such as for display on a user interface or for use in automatically adjusting a parameter of a surgical plan.

Figure 15:
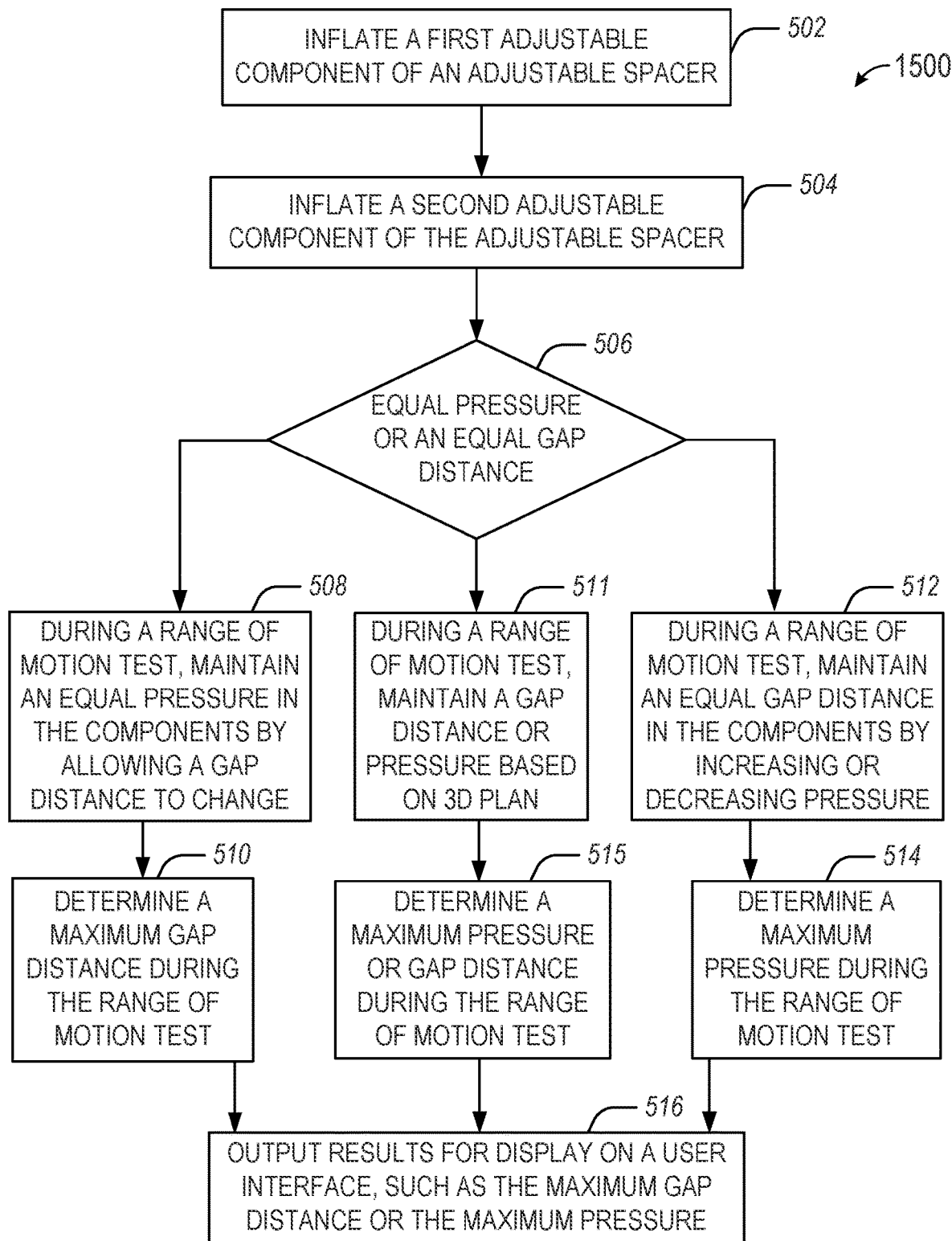
FIG. 15 illustrates a flowchart showing a technique for using an adjustable spacer in a surgical knee procedure in accordance with some embodiments.

FIG. 15 illustrates a flowchart showing a technique 1500 for using an adjustable spacer in a surgical knee procedure in accordance with some embodiments. In an example, the technique 1500 may be performed after an initial tibial cut. In another example, the technique 1500 is performed before any cuts during a knee arthroplasty. The technique 1500 may be performed using a robotic surgical device. The inflation operations described below may be performed using a pump, which may be automatically controlled by a pump controller of the robotic surgical device. The robotic surgical device may include a display to present a user interface for presenting results of the technique 1500.

The technique 1500 includes an operation 502 to inflate a first adjustable component of an adjustable spacer to separate a femur and a tibia of a knee, for example on a medial side of a patient. The technique 1500 includes an operation 504 inflate a second adjustable component of the adjustable spacer to separate the femur and the tibia of the knee, for example on a lateral side of the patient. In an example, the second adjustable component is independently adjustable to the first adjustable component.

The technique 1500 includes an operation 506 to select whether to use an equal pressure or an equal gap distance in the adjustable components. The equal pressure or equal gap distance may be determined using a preoperative plan. The technique 1500 includes an operation 508 when the equal pressure is selected. Operation 508 includes, during a range of motion test, maintaining an equal pressure in the first adjustable component and the second adjustable component by allowing a medial gap distance between the femur and the tibia caused by the first adjustable component or a lateral gap distance between the femur and the tibia the second adjustable component to change.

The technique 1500 includes an operation 510 to, when the equal pressure is selected, determine a maximum gap distance during the range of motion test. The maximum gap distance may be determined using a sensor (e.g., a Hall effect sensor) or using optical tracking of the femur and the tibia. The technique 1500 includes an operation 512 when the equal gap distance is selected. Operation 512 includes, during a range of motion test, maintaining an equal gap distance between a medial gap of the knee caused by the first adjustable component and a lateral gap of the knee caused by the second adjustable component by increasing or decreasing pressure in the first adjustable component or the second adjustable component.

The technique 1500 includes an operation 514 to, when the equal gap distance is selected, determine a maximum pressure during the range of motion test. The maximum pressure may be determined using a sensor (e.g., a pressure sensor such as an eLibra device) or using feedback at a pump used to inflate the components. The technique 1500 includes an operation 516 to output results for display on a user interface, such as the maximum gap distance or the maximum pressure. In another example, results may be used to adjust a preoperative plan. For example, the results may be used to determine an implant based on a maximum gap distance (e.g., lateral or medial or both). The technique 1500 may include repeating a range of motion test, for example after increasing or decreasing the equal pressure or the equal gap distance. In an example, an implant with different heights for each side may be used, for example based on the pressure changes throughout the range of motion.

In an example, the pressure and the gap distance may be allowed to change during the range of motion test. In this example, a 3D plan (e.g., a preoperative plan) may be used to set limits or targets for gap distance or pressure. For example, a maximum pressure may be set for different angles (e.g., from extension to flexion) or a maximum gap may be set. In an example, operation 506 may include a determination to use the 3D plan. The technique 1500 may then proceed to operation 511 to, during a range of motion test, maintain a gap distance or pressure based on the 3D plan. At some portions of the range of motion test, the gap distance may be held constant while at other portions of the range of motion test, the pressure may be held constant, according to the 3D plan. The technique 1500 may include an operation 515 to determine a maximum pressure or maximum gap distance during the range of motion test (e.g., at different portions of the test, based on when the gap distance or the pressure is held constant, respectively).

Figure 16:
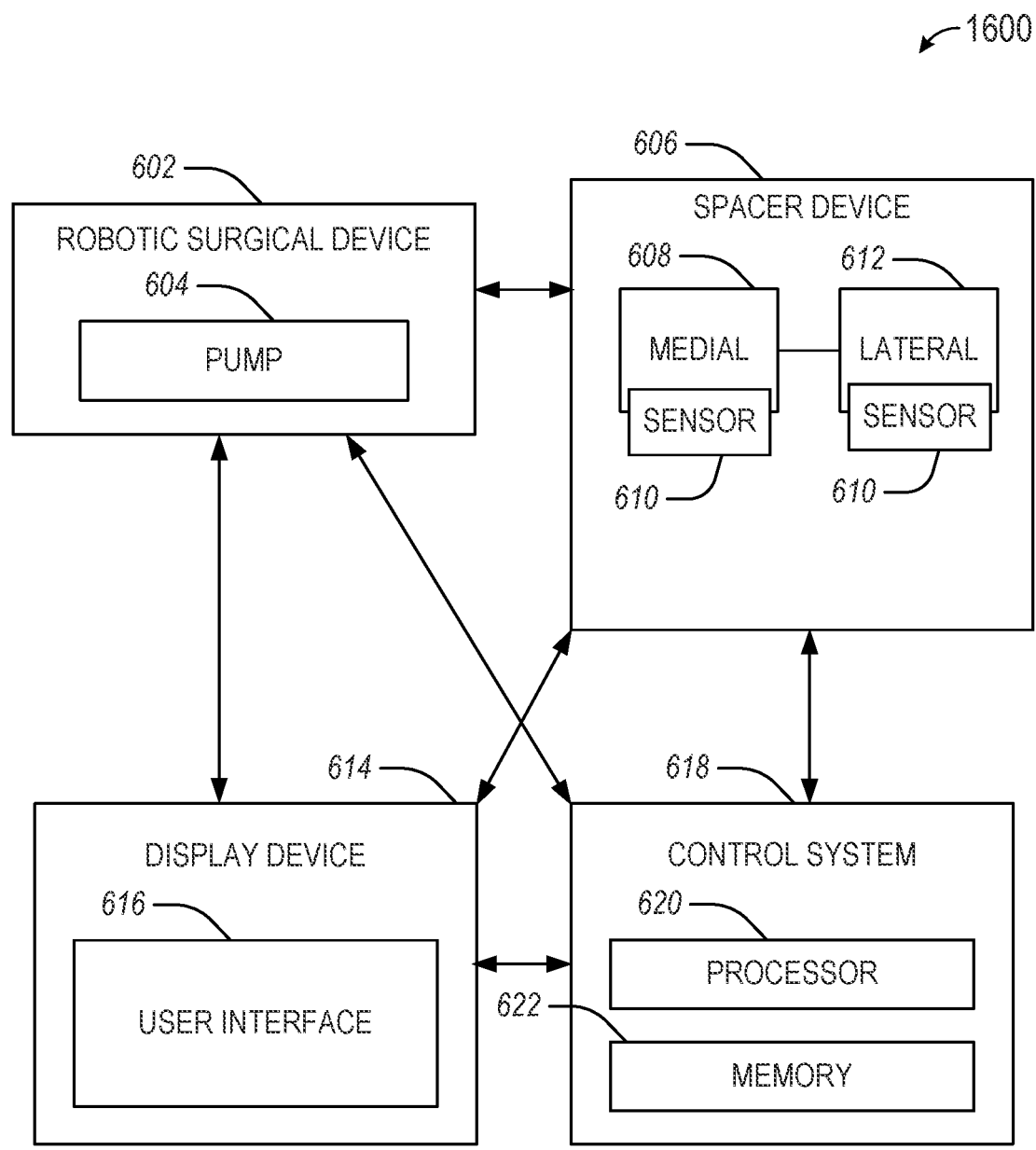
FIG. 16 illustrates a system for performing techniques described herein, in accordance with some embodiments.

FIG. 16 illustrates a system 600 for performing techniques described herein, in accordance with some embodiments. The system 600 includes a robotic surgical device 602 coupled to a pump 604, which may be used to control a spacer device 606. The spacer device 606 includes a medial adjustable component 608 and a lateral adjustable component 612. The system 600 may include a display device 614, which may be used to display a user interface 616. The system 600 may include a control system 618 (e.g., a robotic controller), including a processor 620 and memory 622. In an example, the display device 614 may be coupled to one or more of the robotic surgical device 602, the spacer device 606, or the control system 618.

In an example, the display device 614 may be used to display results of a soft tissue procedure on the user interface 616. The results may include gap distance or pressure information, such as over different angles during a range of motion test. The gap distance or pressure information may be derived from a sensor, such as a sensor 610, which may be on the medial adjustable component 608 or the lateral adjustable component 612 or elsewhere on or within the spacer device 606. The sensor 610 may be a Hall effect sensor. The gap distance or pressure information may be related to a knee joint, and the range of motion test may be performed from extension to flexion (or vice versa).

Figure 17:
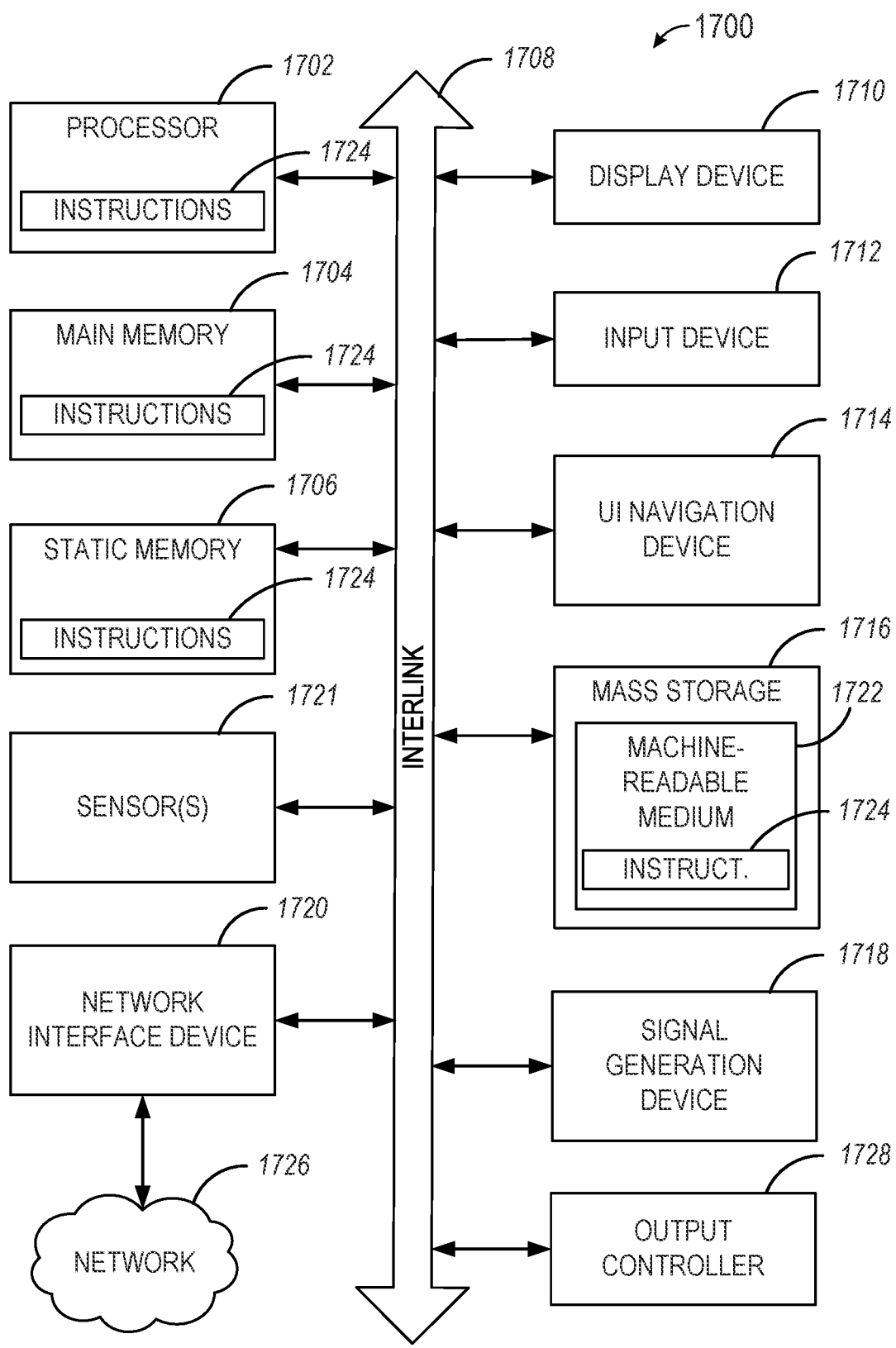
FIG. 17 illustrates a block diagram of an example of a machine upon which any one or more of the techniques discussed herein may perform in accordance with some embodiments.

FIG. 17 illustrates a block diagram of an example machine 1700 upon which any one or more of the techniques discussed herein may perform in accordance with some embodiments. In alternative embodiments, the machine 1700 may operate as a standalone device or may be connected (e.g., networked) to other machines. In a networked deployment, the machine 1700 may operate in the capacity of a server machine, a client machine, or both in server-client network environments. In an example, the machine 1700 may act as a peer machine in peer-to-peer (P2P) (or other distributed) network environment. The machine 1700 may be a personal computer (PC), a tablet PC, a set-top box (SIB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 may include a hardware processor 1702 (e.g., a central processing unit (CPU), a graphics processing unit (GPU), a hardware processor core, or any combination thereof), a main memory 1704 and a static memory 1706, some or all of which may communicate with each other via an interlink (e.g., bus) 1708. The machine 1700 may further include a display unit 1710, an alphanumeric input device 1712 (e.g., a keyboard), and a user interface (UI) navigation device 1714 (e.g., a mouse). In an example, the display unit 1710, input device 1712 and UI navigation device 1714 may be a touch screen display. The machine 1700 may additionally include a storage device (e.g., drive unit) 1716, a signal generation device 1718 (e.g., a speaker), a network interface device 1720, and one or more sensors 1721, such as a global positioning system (GPS) sensor, compass, accelerometer, or other sensor. The machine 1700 may include an output controller 1728, such as a serial (e.g., Universal Serial Bus (USB), parallel, or other wired or wireless e.g., infrared (IR), near field communication (NFC), etc.) connection to communicate or control one or more peripheral devices (e.g., a printer, card reader, etc.).

The storage device 1716 may include a machine readable medium 1722 on which is stored one or more sets of data structures or instructions 1724 (e.g., software) embodying or utilized by any one or more of the techniques or functions described herein. The instructions 1724 may also reside, completely or at least partially, within the main memory 1704, within static memory 1706, or within the hardware processor 1702 during execution thereof by the machine 1700. In an example, one or any combination of the hardware processor 1702, the main memory 1704, the static memory 1706, or the storage device 1716 may constitute machine readable media.

While the machine readable medium 1722 is illustrated as a single medium, the term "machine readable medium" may include a single medium or multiple media (e.g., a centralized or distributed database, and/or associated caches and servers) configured to store the one or more instructions 1724. The term "machine readable medium" may include any medium that is capable of storing, encoding, or carrying instructions for execution by the machine 1700 and that cause the machine 1700 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 1724 may further be transmitted or received over a communications network 1726 using a transmission medium via the network interface device 1720 utilizing any one of a number of transfer protocols (e.g., frame relay, interne protocol (IP), transmission control protocol (TCP), user datagram protocol (LAM), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1720 may include one or more physical jacks (e.g., Ethernet, coaxial, or phone jacks) or one or more antennas to connect to the communications network 1726. In an example, the network interface device 1720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1700, and includes digital or analog communications signals or other intangible medium to facilitate communication of such software.

Each of these non-limiting examples may stand on its own, or may be combined in various permutations or combinations with one or more of the other examples.

Example 1 is a surgical device for evaluating soft tissue during a surgical procedure comprising: a pump to: inflate a first adjustable component of an adjustable spacer to separate a femur and a tibia of a knee on a medial side of a patient; inflate a second adjustable component of the adjustable spacer to separate the femur and the tibia of the knee on a lateral side of the patient, the second adjustable component independently adjustable to the first adjustable component; and during a range of motion test, maintain an equal pressure in the first adjustable component and the second adjustable component by allowing a medial gap distance between the femur and the tibia caused by the first adjustable component or a lateral gap distance between the femur and the tibia the second adjustable component to change; and a processor to: determine a maximum gap distance during the range of motion test; and output the maximum gap distance for display on a user interface.

In Example 2, the subject matter of Example 1 includes, wherein the pump is further to decrease the equal pressure during a repeated range of motion test.

In Example 3, the subject matter of Examples 1-2 includes, wherein the processor is to use a preoperative plan to determine the equal pressure.

In Example 4, the subject matter of Example 3 includes, wherein the processor is further to adjust the preoperative plan based on the maximum gap distance.

In Example 5, the subject matter of Examples 1-4 includes, wherein the range of motion test occurs after a tibial cut during a knee arthroplasty.

In Example 6, the subject matter of Examples 1-5 includes, wherein the processor is further to determine an implant based on a maximum medial gap distance and a maximum lateral gap distance, the implant having a first height for the medial side and a second height different from the first height for the lateral side.

In Example 7, the subject matter of Examples 1-6 includes, wherein to determine the maximum gap distance, the processor is to use optical tracking of the femur and the tibia.

In Example 8, the subject matter of Examples 1-7 includes, wherein the surgical device is a robotic surgical device, wherein the processor operates a robotic controller, wherein the pump is controlled by the processor, and wherein the robotic surgical device includes a display, the display configured to present the user interface including the maximum gap distance.

Example 9 is a surgical device for evaluating soft tissue during a surgical procedure comprising: a pump to: inflate a first adjustable component of an adjustable spacer to separate a femur and a tibia of a knee on a medial side of a patient; inflate a second adjustable component of the adjustable spacer to separate the femur and the tibia of the knee on a lateral side of the patient, the second adjustable component independently adjustable to the first adjustable component; during a range of motion test, maintain an equal gap distance between a medial gap of the knee caused by the first adjustable component and a lateral gap of the knee caused by the second adjustable component by increasing or decreasing pressure in the first adjustable component or the second adjustable component; a processor to: determine a maximum pressure during the range of motion test; and output the maximum pressure for display on a user interface.

In Example 10, the subject matter of Example 9 includes, wherein is further to decrease the equal gap distance and perform the range of motion test again.

In Example 11, the subject matter of Examples 9-10 includes, wherein the processor is to use a preoperative plan used to determine the equal gap distance.

In Example 12, the subject matter of Example 11 includes, wherein the processor is further to adjust the preoperative plan based on the maximum pressure.

In Example 13, the subject matter of Examples 9-12 includes, wherein the range of motion test occurs after a tibial cut during a knee arthroplasty.

In Example 14, the subject matter of Examples 9-13 includes, wherein the processor is further to determine an implant based on a maximum medial pressure and a maximum lateral pressure, the implant having a first height for the medial side and a second height different from the first height for the lateral side.

In Example 15, the subject matter of Examples 9-14 includes, wherein to determine the maximum pressure, the processor is to use optical tracking of the femur and the tibia.

In Example 16, the subject matter of Examples 9-15 includes, wherein the surgical device is a robotic surgical device, wherein the processor operates a robotic controller, wherein the pump is controlled by the processor, and wherein the robotic surgical device includes a display, the display configured to present the user interface including the maximum gap distance.

Example 17 is a method comprising: inserting a trial between a femur and a tibia of a knee, the trial including a medial spacer of a first height and a lateral spacer of a second height differing from the first height; using a pressure sensor device, measuring pressure on a medial side of the knee and a lateral side of the knee throughout a range of motion test with the trial in place; determining a maximum pressure during the range of motion test; and outputting the maximum pressure for display on a user interface.

In Example 18, the subject matter of Example 17 includes, decreasing the first height or the second height by replacing the medial spacer or the lateral spacer and performing the range of motion test again.

In Example 19, the subject matter of Examples 17-18 includes, using a preoperative plan to determine the first height and the second height.

In Example 20, the subject matter of Example 19 includes, adjusting the preoperative plan based on the maximum pressure.

In Example 21, the subject matter of Examples 17-20 includes, performing the range of motion test after a tibial cut during a knee arthroplasty.

In Example 22, the subject matter of Examples 17-21 includes, determining an implant based on a maximum medial pressure and a maximum lateral pressure, the implant having a first height for the medial side and a second height different from the first height for the lateral side.

In Example 23, the subject matter of Examples 17-22 includes, determining the maximum pressure using an iAssist device.

Example 24 is at least one machine-readable medium including instructions that, when executed by processing circuitry, cause the processing circuitry to perform operations to implement of any of Examples 1-23.

Example 25 is an apparatus comprising means to implement of any of Examples 23.

Example 26 is a system to implement of any of Examples 1-23.

Example 27 is a method to implement of any of Examples 1-23.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method, comprising:
providing a robotic surgical system having one or more integral pumps;
initiating a three-dimensional plan of a robotically-assisted total knee arthroplasty using a user interface of the robotic surgical system;
performing a robotically-assisted resection of a tibia of a patient's knee joint to produce a resected surface of the tibia;
inserting an adjustable spacer in between the resected surface of the tibia and a femur of the patient's knee joint;
inserting a force sensor device in between the resected surface of the tibia and the femur of the patient's knee joint;
inflating a first adjustable component of the adjustable spacer using the one or more integral pumps of the robotic surgical system to separate the femur and the tibia on a medial side of the patient's knee joint;
inflating a second adjustable component of the adjustable spacer using the one or more integral pumps of the robotic surgical system to separate the femur and the tibia on a lateral side of the patient's knee joint, the second adjustable component independently adjustable from the first adjustable component;
tracking a degree of flexion or extension of the patient's leg throughout a range of motion test of the patient's knee joint by utilizing an optical tracking system operatively coupled to the robotic surgical system;
maintaining an equal gap distance between a medial gap of the knee caused by the first adjustable component and a lateral gap of the knee caused by the second adjustable component by increasing or decreasing pressure in the first adjustable component or the second adjustable component with the one or more integral pumps of the robotic surgical system;
determining a maximum force between the resected surface of the tibia and the femur during the range of motion test using the force sensor device; and
displaying the maximum force on a display coupled to the robotic surgical system.

2. The method of claim 1, further comprising determining an implant based on the maximum force, and displaying an indication of the implant on the display.

3. The method of claim 1, further comprising decreasing the equal gap distance and performing the range of motion test again.

4. The method of claim 1, further comprising adjusting the three-dimensional plan based on the maximum force.

5. The method of claim 1, wherein maintaining the equal gap distance includes maintaining the equal gap distance during the range of motion test.

6. The method of claim 1, wherein determining the maximum force includes determining a maximum force on the medial side of the patient's knee joint and a maximum force on the lateral side of the patient's knee joint.

7. The method of claim 1, further comprising performing a robotically-assisted resection of a femur of the patient's knee joint, and performing the range of motion test again.

8. The method of claim 1, further comprising displaying the degree of flexion or extension during the range of motion test on the display.

9. A method, comprising:
providing a robotic surgical system having one or more integral pumps;
initiating a three-dimensional plan of a robotically-assisted total knee arthroplasty using a user interface of the robotic surgical system;
performing a robotically-assisted resection of a tibia of a patient's knee joint to produce a resected surface of the tibia;
inserting an adjustable spacer in between the resected surface of the tibia and a femur of the patient's knee joint;
inserting a force sensor device in between the resected surface of the tibia and the femur of the patient's knee joint;
inflating a first adjustable component of the adjustable spacer using the one or more integral pumps of the robotic surgical system to separate the femur and the tibia on the medial side of the patient's knee joint;
inflating a second adjustable component of the adjustable spacer using the one or more integral pumps of the robotic surgical system to separate the femur and the tibia on the lateral side of the patient's knee joint, the second adjustable component independently adjustable from the first adjustable component;
tracking a degree of flexion or extension of the patient's leg throughout a range of motion test of the patient's knee joint by utilizing an optical tracking system operatively coupled to the robotic surgical system;
maintaining an equal pressure between a medial pressure of the knee caused by the first adjustable component and a lateral pressure of the knee caused by the second adjustable component by increasing or decreasing gap distance in the first adjustable component or the second adjustable component with the one or more integral pumps of the robotic surgical system;
determining a maximum gap distance between the resected surface of the tibia and the femur during the range of motion test using the force sensor device; and
displaying the maximum gap distance on a display coupled to the robotic surgical system.

10. The method of claim 9, further comprising determining an implant based on the maximum gap distance, and displaying an indication of the implant on the display.

11. The method of claim 9, further comprising decreasing the equal pressure and performing the range of motion test again.

12. The method of claim 9, further comprising adjusting the three-dimensional plan based on the maximum gap distance.

13. The method of claim 9, wherein maintaining the equal pressure includes maintaining the equal pressure during the range of motion test.

14. The method of claim 9, wherein determining the maximum gap distance includes determining a maximum gap distance on the medial side of the patient's knee joint and a maximum gap distance on the lateral side of the patient's knee joint.

15. The method of claim 9, further comprising performing a robotically-assisted resection of a femur of the patient's knee joint, and performing the range of motion test again.

16. The method of claim 9, further comprising determining the medial pressure of the knee and the lateral pressure of the knee using the using the force sensor device.

17. The method of claim 16, wherein the force sensor device includes a first force sensor on the medial side of the patient's knee joint and a second force sensor on the lateral side of the patient's knee joint.

18. The method of claim 9, further comprising displaying the degree of flexion or extension during the range of motion test on the display.

* * * * *